(12) United States Patent
Do et al.

(10) Patent No.: US 10,991,093 B2
(45) Date of Patent: Apr. 27, 2021

(54) SYSTEMS, METHODS AND MEDIA FOR AUTOMATICALLY GENERATING A BONE AGE ASSESSMENT FROM A RADIOGRAPH

(71) Applicant: THE GENERAL HOSPITAL CORPORATION, Boston, MA (US)

(72) Inventors: Synho Do, Lexington, MA (US); Hyunkwang Lee, Cambridge, MA (US); Michael Gee, Boston, MA (US); Shahein Tajmir, Cambridge, MA (US); Tarik Alkasab, Sudbury, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/334,874

(22) PCT Filed: Sep. 21, 2017

(86) PCT No.: PCT/US2017/052679
§ 371 (c)(1),
(2) Date: Mar. 20, 2019

(87) PCT Pub. No.: WO2018/057714
PCT Pub. Date: Mar. 29, 2018

(65) Prior Publication Data
US 2020/0020097 A1 Jan. 16, 2020

Related U.S. Application Data

(60) Provisional application No. 62/397,667, filed on Sep. 21, 2016.

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/505* (2013.01); *A61B 6/5217* (2013.01); *G06K 9/627* (2013.01);
(Continued)

(58) Field of Classification Search
CPC ...... G06T 7/0012; G16H 10/60; G16H 30/20; G16H 50/20; G16H 30/40; G06K 9/6256;
(Continued)

(56) References Cited

U.S. PATENT DOCUMENTS 7,848,893 B2 12/2010 Thodberg
2003/0065264 A1 4/2003 Tsoref et al.
(Continued)

OTHER PUBLICATIONS

Anthimopoulos et al., Lung Pattern Classification for Interstitial Lung Diseases Using a Deep Convolutional Neural Network, IEEE Transactions on Medical Imaging, 2016, 35(5):1207-1216.
(Continued)

*Primary Examiner* — Stephen P Coleman
(74) *Attorney, Agent, or Firm* — Quarles & Brady LLP

(57) ABSTRACT

In accordance with some embodiments, systems, methods and media for generating a bone age assessment. In some embodiments, a method comprises: receiving an x-ray image of a subject's left hand and wrist; converting the image to a predetermined size; identifying, without user intervention, a first portion of the image corresponding to the hand and wrist; processing the first portion of the image to increase contrast between bones and non-bones to generate a processed image; causing a trained convolution neural network to determine a bone age based on the processed image; receiving an indication of the bone age; causing the bone age to be presented to a user as the result of a bone age
(Continued)

assessment; and causing the bone age and the image to be stored in an electronic medical record associated with the subject.

21 Claims, 14 Drawing Sheets

(51) Int. Cl.
```
G16H 10/60      (2018.01)
G16H 30/20      (2018.01)
G16H 50/20      (2018.01)
G16H 30/40      (2018.01)
A61B 6/00       (2006.01)
G06K 9/62       (2006.01)
G06N 3/04       (2006.01)
G06N 3/08       (2006.01)
A61B 5/00       (2006.01)
```
(52) U.S. Cl.
CPC ......... *G06K 9/6256* (2013.01); *G06N 3/0454* (2013.01); *G06N 3/08* (2013.01); *G16H 10/60* (2018.01); *G16H 30/20* (2018.01); *G16H 30/40* (2018.01); *G16H 50/20* (2018.01); *A61B 5/4509* (2013.01); *G06K 2209/055* (2013.01); *G06T 2207/10116* (2013.01); *G06T 2207/20081* (2013.01); *G06T 2207/20084* (2013.01); *G06T 2207/30008* (2013.01)

(58) Field of Classification Search
CPC ........ G06K 9/627; G06N 3/0454; G06N 3/08; A61B 6/505; A61B 6/5217
USPC ....................................................... 382/132
See application file for complete search history.

(56) References Cited

U.S. PATENT DOCUMENTS

| | | | |
|---|---|---|---|
| 2005/0196031 A1* | 9/2005 | Hsieh ................. | G06K 9/00067 382/132 |
| 2011/0058726 A1 | 3/2011 | Markwardt et al. | |
| 2015/0065803 A1* | 3/2015 | Douglas .................... | G06T 7/11 600/200 |

OTHER PUBLICATIONS

Canziani et al., An Analysis of Deep Neural Network Models for Practical Applications, 2017, arXiv:1605.07678, 7 pages.
Deng et al., ImageNet: A Large-Scale Hierarchical Image Database, In 2009 IEEE Conference on Computer Vision and Pattern Recognition, 2009, pp. 248-255.
Deng et al., Leveraging the Wisdom of the Crowd for Fine-Grained Recognition, IEEE Transactions on Pattern Analysis and Machine Intelligence, 2016, 38(4):666-676.
Gilsanz et al., eBook: Hand Bone Age—A Digital Atlas of Skeletal Maturity, Copyright Springer-Verlag Berlin Heidelberg 2005, 106 pages.
Girshick et al., Rich Feature Hierarchies for Accurate Object Detection and Semantic Segmentation, In Proceedings of the IEEE Conference on Computer Vision and Pattern Recognition, 2014, pp. 580-587.
Greenspan et al., Guest Editorial—Deep Learning in Medical Imaging: Overview and Future Promise of an Exciting New Technique, IEEE Transactions on Medical Imaging, 2016, 35(5):1153-1159.
He, et al., Deep Residual Learning for Image Recognition, 2015, arXiv:1512.03385, 12 pages.
Heyworth et al., A New, Validated Shorthand Method for Determining Bone Age, Annual Meeting of the American Academy of Orthopaedic Surgeons, 2011, https://web.archive.org/web/20121124123319/https://www.hss.edu/files/hssboneageposter.pdf, 1 page.
Krizhevsky et al., ImageNet Classification with Deep Convolutional Neural Networks, Advances in Neural Information Processing Systems, 2012, pp. 1097-1105.
Lecun, et al., Gradient-Based Learning Applied to Document Recognition, Proceedings of the IEEE, 1998, 86(11):2278-2324.
Lecun et al., The MNIST Database of Handwritten Digits, http://yann.lecun.com/exdb/mnist/, 1998, 8 pages.
Lecun et al., Deep Learning, Nature, 2015, 521(7553):436-444.
Liskowski et al., Segmenting Retinal Blood Vessels with Deep Neural Networks, IEEE Transactions on Medical Imaging, 2016, 35(11):2369-2380.
Nilsback et al., Automated Flower Classification Over a Large Number of Classes, In 2008 Sixth Indian Conference on Computer Vision, Graphics & Image Processing, IEEE, 2008, pp. 722-729.
Oestreich, Review of "Hand Bone Age: A Digital Atlas of Skeletal Maturity", Radiographics, 2005, 25:1074.
Russakovsky et al., ImageNet Large Scale Visual Recognition Challenge (ILSVRC) 2013: Introduction, Presentation, 35 pages.
Russakovsky et al., ImageNet Large Scale Visual Recognition Challenge, International Journal of Computer Vision, 2015, 115(3):211-252.
Seok et al., Automated Classification System for Bone Age X-ray Images, In 2012 IEEE International Conference on Systems, Man, and Cybernetics (SMC), pp. 208-213.
Shin et al., Deep Convolutional Neural Networks for Computer-Aided Detection: CNN Architectures, Dataset Characteristics and Transfer Learning, IEEE Transactions on Medical Imaging, 2016, 35(5):1285-1298.
Simonyan et al., Deep Inside Convolutional Networks: Visualising Image Classification Models and Saliency Maps, 2013, arXiv:1312.6034, 8 pages.
Simonyan et al., Very Deep Convolutional Networks for Large-Scale Image Recognition, arXiv:1409.1556v6, 2015, 14 pages.
Somkantha et al., Bone Age Assessment in Young Children Using Automatic Carpal Bone Feature Extraction and Support Vector Regression, Journal of Digital Imaging, 2011, 24(6):1044-1058.
Szegedy et al., Going Deeper with Convolutions, In Proceedings of the IEEE Conference on Computer Vision and Pattern Recognition, 2015, pp. 1-9.
Tajbakhsh et al., Convolutional Neural Networks for Medical Image Analysis: Full Training or Fine Tuning?, IEEE Transactions on Medical Imaging, 2016, 35(5):1299-1312.
Thodberg et al., The BoneXpert Method for Automated Determination of Skeletal Maturity, IEEE Transactions on Medical Imaging, 2009, 28(1):52-66.
Van Grinsven et al., Fast Convolutional Neural Network Training Using Selective Data Sampling: Application to Hemorrhage Detection in Color Fundus Images, IEEE Transactions on Medical Imaging, 2016, 35(5):1273-1284.
Wah et al., The Caltech-UCSD Birds-200-2011 Dataset, Pasadena, CA: California Institute of Technology, 2011, 8 pages.
Yan et al., Multi-Instance Deep Learning: Discover Discriminative Local Anatomies for Bodypart Recognition, IEEE Transactions on Medical Imaging, 2016, 35(5):1332-1343.
Zeiler et al., Visualizing and Understanding Convolutional Networks, In European Conference on Computer Vision, 2014, Part I, LNCS 8689, pp. 818-833.
Zhang et al., Automatic Bone Age Assessment for Young Children from Newborn to 7-year-old Using Carpal Bones, computerized Medical Imaging and Graphics, 2007, 31(4-5):299-310.
Zhang et al., Maturation Disparity Between Hand-Wrist Bones in a Chinese Sample of Normal Children: An Analysis Based on Automatic BoneXpert and Manual Greulich and Pyle Atlas Assessment, Korean Journal of Radiology, 2016, 17(3):435-442.
PCT International Search Report and Written Opinion, PCT/US2017/052679, dated Nov. 7, 2017, 12 pages.

* cited by examiner

SYSTEMS, METHODS AND MEDIA FOR AUTOMATICALLY GENERATING A BONE AGE ASSESSMENT FROM A RADIOGRAPH

CROSS-REFERENCE TO RELATED APPLICATIONS

This application represents the national stage entry of PCT International Application No. PCT/US2017/052679 filed Sep. 21, 2017, which is based on, claims the benefit of, and claims priority to U.S. Provisional Application No. 62/397,667, filed Sep. 21, 2016, which is hereby incorporated herein by reference in its entirety for all purposes.

STATEMENT REGARDING FEDERALLY SPONSORED RESEARCH

N/A

BACKGROUND

Skeletal maturity progresses through a series of discrete phases, particularly in the wrist and hands. Pediatric medicine has used this regular progression of growth to assign a bone age and correlate it with a child's chronological age. If there are discrepancies between chronological age and bone age, the discrepancy can help direct further diagnostic evaluation of possible endocrine or metabolic disorders. Alternatively, determinations of bone age may be used to time interventions to treat limb-length discrepancies. While the process of bone age assessment is central to the evaluation of many disease states, the actual process has not changed significantly since the publication, by Greulich and Pyle, of the groundbreaking atlas in 1950, which was developed from studying children in Ohio from 1931-42. In general, as shown in FIG. 1, manual bone age assessment is performed by opening or otherwise accessing a radiograph of the left wrist and hand of the patient, opening (or otherwise accessing) the atlas of images, comparing the bones shown in the radiograph to the bones shown in the atlas corresponding to various bone ages, assessing the bone age based on the subjective comparisons, and generating a report indicating the bone age determined by the evaluator. Such reports may vary widely in how the bone age is recorded (e.g., as one number, as a range, with or without information about the evaluators confidence in the assessment, etc.).

Bone age analysis can be performed using the Greulich and Pyle (GP) or Tanner-Whitehouse (TW2) methods. For example, the GP method compares the patient's radiograph with an atlas of representative ages to determine the bone age, while the TW2 method is based on a scoring system that examines 20 specific bones. In both cases, however, bone age assessment requires considerable time and contains significant interrater variability, leading to clinical challenges when therapy decisions are made based on changes in a patient's bone age assessment. While attempts have been made to shorten the manual evaluation process by defining shorthand methods, these still rely on human interpretation and reference to an atlas.

Fully automated BAA has been a goal of computer vision and radiology research for many years. While bone-age assessment would seem to be an ideal target for automated image evaluation because there are few images in a single study (i.e., one image of the left hand and wrist) and relatively standardized reported findings (all reports contain chronological and bone ages with relatively standardized keywords, like "bone age" or "year old"). However, most prior approaches have significant limitations that limit their usefulness. For example, most prior approaches have included classification or regression using hand-crafted features extracted from Regions of Interest (ROIs) for specific bones segmented by computer algorithms. TABLE 1, below, summarizes three prior attempts at automated bone age analysis.

TABLE 1

| Dataset | Method | Features | Limitations |
| --- | --- | --- | --- |
| 24 Images | SIFT, SVD Fully-connected neural network | Fixed-size feature vectors from SIFT descriptors with SVD | Training and validation with limited data Deficiency of robustness to actual images |
| 180 Images | Canny edge detection SVM | Morphological features regarding carpal bones | Not applicable for children older than 7 years |
| 1559 Images | AAM PCA | Features regarding shape, intensity, texture of RUS bones | Vulnerable to excessive noise in images Chronological age used as input |

One technique (proposed by Seok et al., "Automated Classification System for Bone Age X-ray Images," 2012 IEEE International Conference on Systems, Man, and Cybernetics, 2012) utilized a Scale Invariant Feature Transform (SIFT) to extract image descriptors and Singular Value Decomposition (SVD) to create fixed-size feature vectors. These were fed into a fully connected neural network. Since only a small number of images were used, the model was not robust to images that were totally different from the training dataset. There were also no quantifiable performance metrics available. As another example, another technique (proposed by Somkantha, et al., "Bone Age Assessment in Young Children Using Automatic Carpal Bone Feature Extraction and Support Vector Regression," J Digit Imaging, 24: 1044, 2011) selected the carpal bone region using projections in both the horizontal and vertical axes, extracting boundaries of the carpal bones. Five morphological features were extracted from the segmented carpal bones and used for regression with a Support Vector Machine (SVM). This approach is similar to another approach (proposed by Zhang et al., "Automatic Bone Age Assessment for Young Children from Newborn to 7-year-old Using Carpal Bones," Computerized Medical Imaging and Graphics, 31:299, 2007), in that hand-engineered features were extracted from carpal bones, and the features were used as input for a fuzzy logic classifier. However, this approach is not applicable for children older than 5 to 7 years as the carpal bones are typically fully mature by that age and no longer allow meaningful discrimination beyond that point.

One of the more successful attempts has been BoneXpert (described in Thodberg, et al., "The BoneXpert Method for Automated Determination of Skeletal Maturity," IEEE Transactions in Medical Imaging, Vol. 28, Issue 1, pp. 52-66, 2008), a software only medical device approved for use in Europe and the first commercial implementation of automated bone age assessment. BoneXpert utilizes a generative model, the Active Appearance Model (AAM), to automatically segment 15 bones in the hand and wrist and then determine either the GP or TW2 bone age based on shape, intensity, and textural features. While BoneXpert reports considerable accuracy for automated bone age assessment, it has several critical limitations. For example, BoneXpert does not identify bone age directly, because the prediction depends on a relationship between chronological and bone ages. Additionally, BoneXpert is not robust and rejects radiographs when there is excessive noise. In one example, BoneXpert rejected around 235 individual bones out of 5161 (or 4.5%). Finally, BoneXpert does not utilize the carpal bones, despite their containing discriminative features for young children.

In summary, all prior attempts at automated BAA are based on hand-crafted features, reducing the capability of the algorithms from generalizing to the target application. Unfortunately, all prior approaches used varying datasets and made only limited implementation and parameter selection details available, making a fair comparison with prior conventional approaches impossible.

Accordingly, systems, methods, and media for automatically generating a bone age assessment from a radiograph are desirable.

SUMMARY

In accordance with some embodiments of the disclosed subject matter, systems, methods, and media for automatically generating a bone age assessment from a radiograph are provided.

In accordance with some embodiments of the disclosed subject matter, a system for generating a bone age assessment is provided, the system comprising: at least one hardware processor that is programmed to: receive an image that includes a subject's left hand and wrist including a plurality of bones; convert the image to a predetermined size; identify, without user intervention, a first portion of the image that corresponds to the subject's hand and wrist; process the first portion of the image to increase contrast between image corresponding to the plurality of bones, and image data that does not correspond to bones to generate a processed image; cause a trained convolution neural network to determine a most likely bone age represented by the plurality of bones based on the processed image; receive an indication of the most likely bone age represented by the one or more bones; cause the most likely bone age to be presented to a user as the result of a bone age assessment; and cause the most likely bone age and the image to be stored in an electronic medical record associated with the subject.

In some embodiments, the at least one hardware processor is further programmed to: cause a second trained convolution neural network to classify a first patch of a second predetermined size, including a first pixel, from the image to determine the likelihood that the first patch includes hand; cause the second trained convolution neural network to classify a second patch of the second predetermined size, including the first pixel, from the image to determine the likelihood that the second patch includes hand; label the first pixel as hand based on the likelihood that the first patch includes hand and the likelihood that the second patch includes hand; label a plurality of pixels as corresponding to hand; and label a second plurality of pixels as not corresponding to hand.

In some embodiments, the at least one hardware processor is further programmed to: identify a largest group of contiguous pixels labeled as hand based on labels corresponding to the first pixel and the plurality of pixels; generate a mask based on the largest group of continuous pixels; remove image data that does not correspond to the mask; and center the image that corresponds to the mask.

In some embodiments, the second trained convolution neural network outputs a plurality of likelihoods each corresponding to the presence of a particular type of object in a patch of the second predetermined size, wherein a first likelihood corresponds to the presence of bone, a second likelihood corresponds to the presence of tissue, and the likelihood that a patch includes hand is the sum of the first likelihood and the second likelihood.

In some embodiments, the at least one hardware processor is further programmed to: receive a set of training images each corresponding to a radiograph of a hand; receive, for each training image, bone age information indicating the bone age represented in the training image; convert each training image to the predetermined size; determine a background color of each training image; convert a first training image included in the set of training images that has a light background and dark bones to a first normalized training image that has a dark background and light bones; extract a plurality of samples from a subset of training images included in the set of training images, wherein each sample is a second predetermined size, and corresponds to one of a plurality of object classes; label each of the plurality samples as corresponding to one of the plurality of object classes; train a second convolution neural network to determine the likelihood that a submitted patch of the second predetermined size is a member of each of the plurality of object classes using the labeled plurality of samples as training data; provide a first training image of the predetermined size from the set of training images to the second convolution neural network; identify a first portion of the first training image that corresponds to hand based on output of the second convolution neural network; process the first portion to increase contrast between image data corresponding to bones in the first training image and image data that does not correspond to bones to generate a first processed image; and train the convolution neural network using the first processed image and bone age information indicating the bone age represented in the first training image.

In some embodiments, the at least one hardware processor is further programmed to: initialize the convolution neural network with a pre-trained model generated using natural images; and fine-tune one or more hyperparameters of the pre-trained model using the first processed image and bone age information indicating the bone age represented in the first training image.

In some embodiments, the system is a first computing device connected as part of a local area network, the at least one hardware processor is further programmed to: receive the image from a second computing device connected as part of the local area network; send the processed image to a remote server that hosts the trained neural network over a wide area network.

In some embodiments, the system is a first computing device connected as part of a local area network, the at least one hardware processor is further programmed to: receive the image from a second computing device connected as part of the local area network; and execute the trained neural network to determine the most likely bone age represented by the plurality of bones.

In some embodiments, the at least one hardware processor is further programmed to receive the trained neural network from a remote server over a wide area network.

In some embodiments, the at least one hardware processor is further programmed to: cause the most likely bone age to be presented to the user with a plurality of representative images including a first image that includes features corresponding to the most likely bone age, a second image that includes features corresponding to a second most likely bone age, and a third image that includes features corresponding to a third most likely bone age; prompt the user to select a bone age represented in the image; and cause the most likely bone age, the image, and the selected bone age to be stored in the electronic medical record.

In accordance with some embodiments of the disclosed subject matter, a method for generating a bone age assessment is provided, the method comprising: receiving an image that includes a subject's left hand and wrist including a plurality of bones; converting the image to a predetermined size; identifying, without user intervention, a first portion of the image that corresponds to the subject's hand and wrist; processing the first portion of the image to increase contrast between image corresponding to the plurality of bones, and image data that does not correspond to bones to generate a processed image; causing a trained convolution neural network to determine a most likely bone age represented by the plurality of bones based on the processed image; receiving an indication of the most likely bone age represented by the one or more bones; causing the most likely bone age to be presented to a user as the result of a bone age assessment; and causing the most likely bone age and the image to be stored in an electronic medical record associated with the subject.

In accordance with some embodiments of the disclosed subject matter, a non-transitory computer readable medium containing computer executable instructions that, when executed by a processor, cause the processor to perform a method for generating a bone age assessment is provided, the method comprising: receiving an image that includes a subject's left hand and wrist including a plurality of bones; converting the image to a predetermined size; identifying, without user intervention, a first portion of the image that corresponds to the subject's hand and wrist; processing the first portion of the image to increase contrast between image corresponding to the plurality of bones, and image data that does not correspond to bones to generate a processed image; causing a trained convolution neural network to determine a most likely bone age represented by the plurality of bones based on the processed image; receiving an indication of the most likely bone age represented by the one or more bones; causing the most likely bone age to be presented to a user as the result of a bone age assessment; and causing the most likely bone age and the image to be stored in an electronic medical record associated with the subject.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

Figure 1:
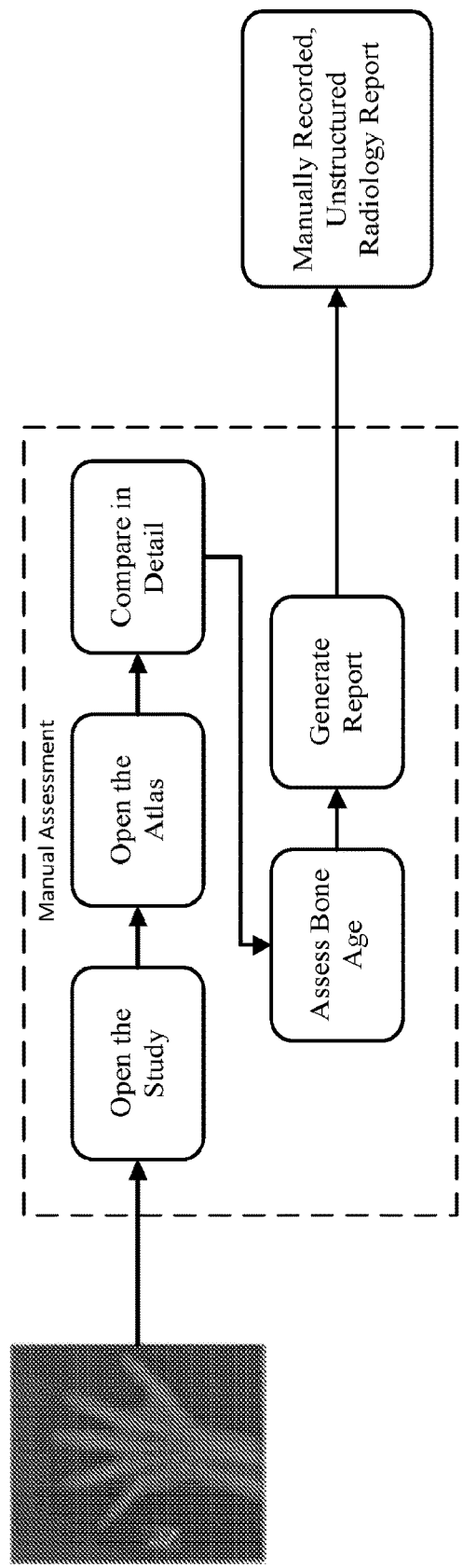
FIG. 1 shows an example of a manual technique for determining bone age.

In accordance with various embodiments, mechanisms (which can, for example, include systems, methods, and media) for automatically generating a bone age assessment from a radiograph are provided.

In general, deep learning is a powerful technique for a wide range of computer vision image tasks, leading to growing interest in using the technique to replace conventional algorithms using manually crafted features. From using deep CNNs to detect patterns of interstitial lung disease on 2D patches of chest CTs, to segmenting the vascular network of the human eye on fundus photos, deep CNNs have proven enormously successful because they enable learning highly representative, layered, hierarchical abstractions from image data. In addition to segmentation and detection tasks, many deep learning-based techniques are well suited for recognition and classification tasks in medical imaging. However, a data-driven, deep learning approach has not been introduced to reduce human expert interobserver variability and improve workflow efficiency of bone age assessment. In some embodiments, the mechanisms described herein can train a fully-automated deep learning system to perform bone age analysis using deep CNNs for detection and classification to automatically generate structured radiology reports.

Many innovative deep neural networks and novel training methods have demonstrated impressive performance for image classification tasks, most notably in the ImageNet competition. The rapid advance in classification of natural images has been assisted by the availability of large-scale and comprehensively-annotated datasets such as ImageNet. However, obtaining medical datasets on such scale and with equal quality annotation remains a challenge. For example, medical data cannot be easily accessed due to patient privacy regulations (e.g., HIPAA), and image annotation requires an onerous and time-consuming effort of highly trained human experts (e.g., radiologists). Further, most classification problems in the medical imaging domain are fine-grained recognition tasks which classify highly similar appearing objects in the same class using local discriminative features. This makes the dearth of available training data more problematic, as such fine-grained discrimination would normally require a very large data set.

In some embodiments, the mechanisms described herein can retrieve and process a set of training images to be used to train a classification CNN to automatically classify bone age using only a received radiograph. For example, the mechanisms can retrieve a set of training radiographs and corresponding radiology reports listing bone age determined by a human expert from electronic medical records maintained by one or more health providers (in accordance with procedures required by regulations, such as HIPAA).

In some embodiments, the mechanisms described herein can process the training radiographs to normalize the appearance of each radiograph, and enhance the appearance of bones in the processed image. For example, the mechanisms can convert all radiographs to a common grayscale base (e.g., white background or black background), a common size, etc., and can use one or more image processing techniques to accentuate the bones in the processed radiograph.

In some embodiments, the processed training images can be used, with the bone ages extracted from corresponding radiology reports, to train a classification CNN. For example, the mechanisms can use the training data set to fine-tune hyperparameters in one or more layers of a trained generic image classification CNN.

In some embodiments, after training the classification CNN, the mechanisms described herein can use the trained CNN to determine the bone age in radiographs. For example, the mechanisms can receive a radiograph to be analyzed, can process the image to provide a normalized and processed image for submission to the trained classification CNN, and can receive a bone age assessment without user input.

Figure 2:
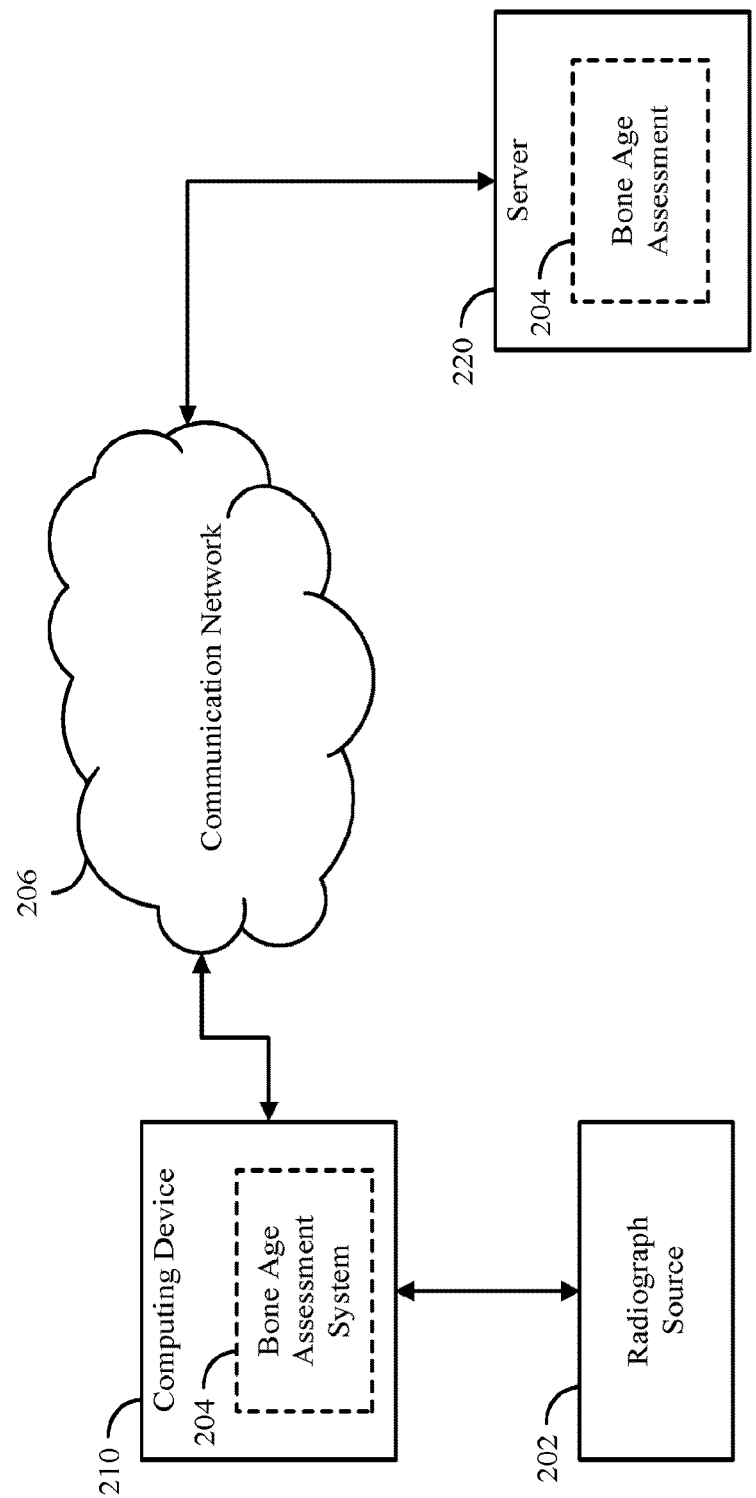
FIG. 2 shows an example of a system for automatically generating a bone age assessment from a radiograph is shown in accordance with some embodiments of the disclosed subject matter.

Turning to FIG. 2, an example 200 of a system for automatically generating a bone age assessment from a radiograph is shown in accordance with some embodiments of the disclosed subject matter. As shown in FIG. 2, a computing device 210 can receive one or more radiographs from a radiograph source 202. In some embodiments, computing device 210 can execute at least a portion of a bone age assessment system 204 to generate a bone age assessment based on a radiograph received from radiograph source 202. Additionally or alternatively, in some embodiments, computing device 210 can communicate information about the radiograph received from radiograph source 202 to a server 220 over a communication network 206, which can execute at least a portion of bone age assessment system 204 to generate a bone age assessment based on the radiograph. In some such embodiments, server 220 can return information to computing device 210 (and/or any other suitable computing device) indicative of an output of bone age assessment system 204, such as a bone age determined from the radiograph, a report regarding the bone age determined from the radiograph, etc. In some embodiments, computing device 210 and/or server 220 can be any suitable computing device or combination of devices, such as a desktop computer, a laptop computer, a smartphone, a tablet computer, a wearable computer, a server computer, a virtual machine being executed by a physical computing device, etc. As described below in connection with FIGS. 4-9, bone age assessment system 204 can use one or more trained convolution neural networks to determine a bone age associated with the radiograph, and can present information about the determined bone age to a user (e.g., a physician).

In some embodiments, radiograph source 202 can be any suitable source of radiograph information, such as a digital x-ray machine, an x-ray film scanner, another computing device (e.g., a server storing one or more radiographs), etc. In some embodiments, radiograph source 202 can be local to computing device 210. For example, radiograph source 202 can be incorporated with computing device 210 (e.g., computing device 210 can be configured as part of a device for capturing, scanning, and/or storing radiographs). As another example, radiograph source 202 can be connected to computing device 210 by a cable, a direct wireless link, etc. Additionally or alternatively, in some embodiments, radiograph source 202 can be located locally and/or remotely from computing device 210, and can communicate radiographic information to computing device 210 (and/or server 220) via a communication network (e.g., communication network 206).

In some embodiments, communication network 206 can be any suitable communication network or combination of communication networks. For example, communication network 206 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 206 can be a local area network, a wide area network, a public network (e.g., the Internet), a private or semi-private network (e.g., a corporate or university intranet), any other suitable type of network, or any suitable combination of networks. Communications links shown in FIG. 2 can each be any suitable communications link or combination of communications links, such as wired links, fiber optic links, Wi-Fi links, Bluetooth links, cellular links, etc.

Figure 3:
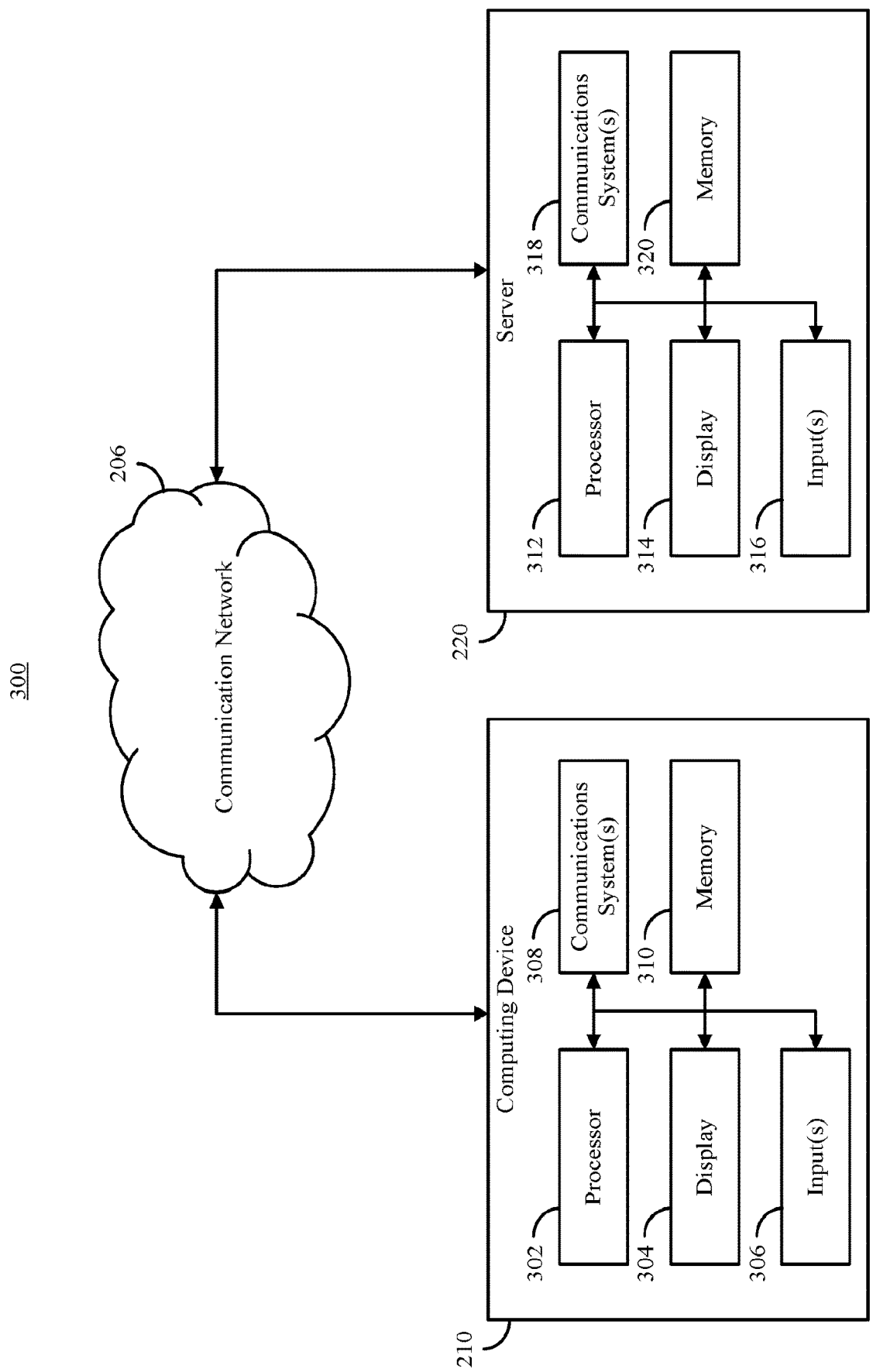
FIG. 3 shows an example of hardware that can be used to implement computing device and server in accordance with some embodiments of the disclosed subject matter.

FIG. 3 shows an example 300 of hardware that can be used to implement computing device 210 and server 230 in accordance with some embodiments of the disclosed subject matter. As shown in FIG. 3, in some embodiments, computing device 210 can include a processor 302, a display 304, one or more inputs 306, one or more communication systems 308, and/or memory 310. In some embodiments, processor 302 can be any suitable hardware processor or combination of processors, such as a central processing unit, a graphics processing unit, etc. In some embodiments, display 304 can include any suitable display devices, such as a computer monitor, a touchscreen, a television, etc. In some embodiments, inputs 306 can include any suitable input devices and/or sensors that can be used to receive user input, such as a keyboard, a mouse, a touchscreen, a microphone, etc.

In some embodiments, communications systems 308 can include any suitable hardware, firmware, and/or software for communicating information over communication network 206 and/or any other suitable communication networks. For example, communications systems 308 can include one or more transceivers, one or more communication chips and/or chip sets, etc. In a more particular example, communications systems 308 can include hardware, firmware and/or software that can be used to establish a Wi-Fi connection, a Bluetooth connection, a cellular connection, an Ethernet connection, etc.

In some embodiments, memory 310 can include any suitable storage device or devices that can be used to store instructions, values, etc., that can be used, for example, by processor 302 to present content using display 304, to communicate with server 220 via communications system(s) 308, etc. Memory 310 can include any suitable volatile memory, non-volatile memory, storage, or any suitable combination thereof. For example, memory 310 can include RAM, ROM, EEPROM, one or more flash drives, one or more hard disks, one or more solid state drives, one or more optical drives, etc. In some embodiments, memory 310 can have encoded thereon a computer program for controlling operation of computing device 210. In such embodiments, processor 302 can execute at least a portion of the computer program to present content (e.g., images, user interfaces, graphics, tables, etc.), receive content from server 220, transmit information to server 220, etc.

In some embodiments, server 220 can include a processor 312, a display 314, one or more inputs 316, one or more communications systems 318, and/or memory 320. In some embodiments, processor 312 can be any suitable hardware processor or combination of processors, such as a central processing unit, a graphics processing unit, etc. In some embodiments, display 314 can include any suitable display devices, such as a computer monitor, a touchscreen, a television, etc. In some embodiments, inputs 316 can include any suitable input devices and/or sensors that can be used to receive user input, such as a keyboard, a mouse, a touchscreen, a microphone, etc.

In some embodiments, communications systems 318 can include any suitable hardware, firmware, and/or software for communicating information over communication network 206 and/or any other suitable communication networks. For example, communications systems 318 can include one or more transceivers, one or more communication chips and/or chip sets, etc. In a more particular example, communications systems 318 can include hardware, firmware and/or software that can be used to establish a Wi-Fi connection, a Bluetooth connection, a cellular connection, an Ethernet connection, etc.

In some embodiments, memory 320 can include any suitable storage device or devices that can be used to store instructions, values, etc., that can be used, for example, by processor 312 to present content using display 314, to communicate with one or more computing devices 210, etc. Memory 320 can include any suitable volatile memory, non-volatile memory, storage, or any suitable combination thereof. For example, memory 320 can include RAM, ROM, EEPROM, one or more flash drives, one or more hard disks, one or more solid state drives, one or more optical drives, etc. In some embodiments, memory 320 can have encoded thereon a server program for controlling operation of server 220. In such embodiments, processor 312 can execute at least a portion of the server program to transmit information and/or content (e.g., results of a bone age assessment, a user interface, etc.) to one or more computing devices 210, receive information and/or content from one or more computing devices 210, receive instructions from one or more devices (e.g., a personal computer, a laptop computer, a tablet computer, a smartphone, etc.), etc.

Figure 4:
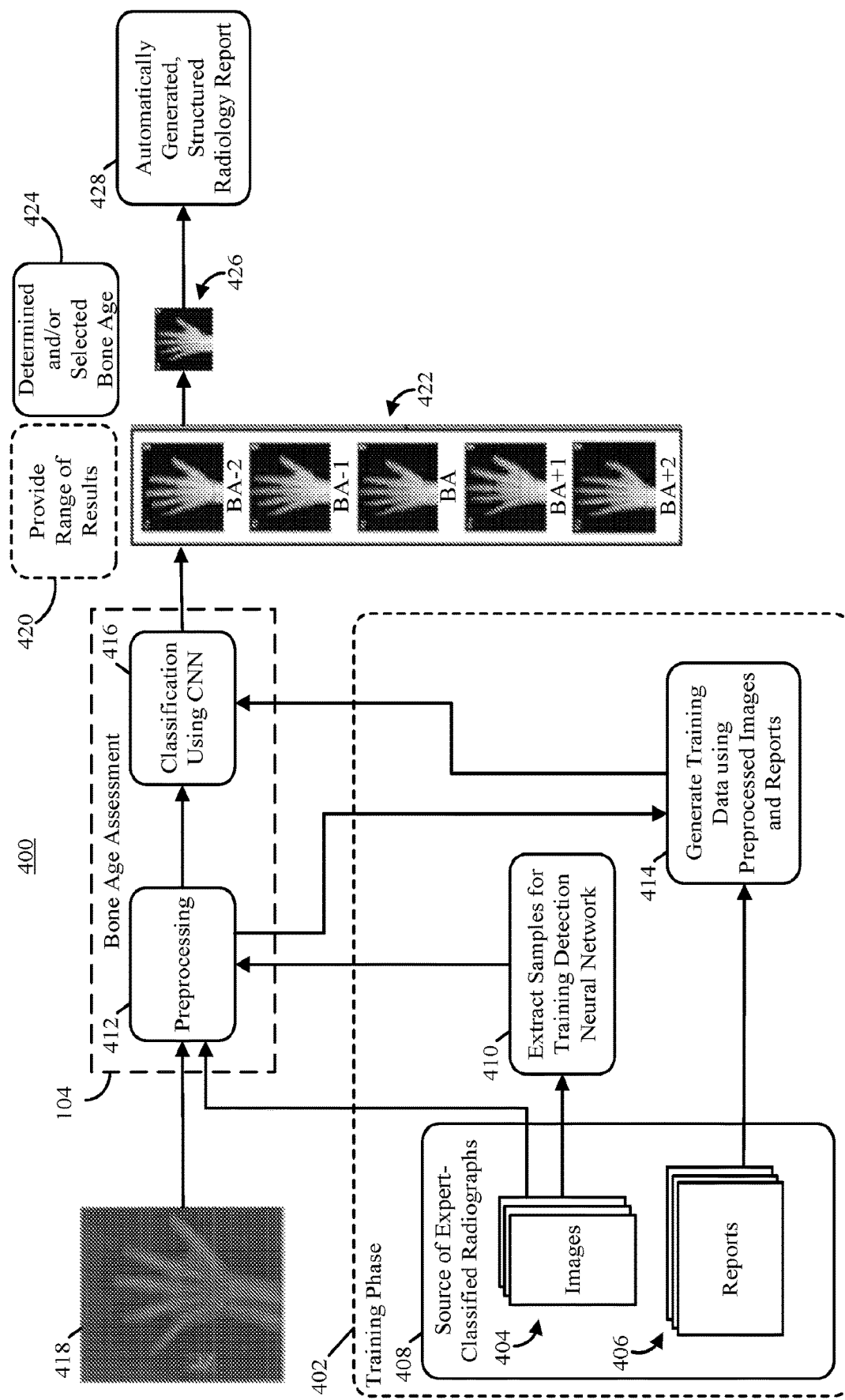
FIG. 4 shows an example of a flow for training and using mechanisms for automatically generating a bone age assessment from a radiograph in accordance with some embodiments of the disclosed subject matter.

FIG. 4 shows an example 400 of a flow for training and using mechanisms for automatically generating a bone age assessment from a radiograph in accordance with some embodiments of the disclosed subject matter. As shown in FIG. 4, during a training phase 402, radiograph images 404 and corresponding radiology reports 406 from a source of expert-classified radiographs 408 (or multiple sources of expert-classified radiographs) can be used to train bone assessment system 104. In some embodiments, radiograph source 408 can be any suitable source of radiographs and corresponding reports that include bone age assessments based on the radiographs. For example, radiograph images 404 and corresponding radiology reports 406 can be retrieved from the electronic medical records maintained by one or more medical providers. As another example, radiograph images 404 can be obtained (e.g., by performing an x-ray, by retrieving the images from electronic medical records, etc.), and corresponding radiology reports 406 can be generated by a radiologist examining the radiographs to determine a bone age represented in the radiograph.

At 410, samples (e.g., representing a region of interest) can be taken from at least a portion of the radiographs representing various types of objects that are likely to be present in radiographs used to conduct a bone age assessment. For example, a radiograph image used to determine the bone age of the subject of the radiograph is likely to include areas representing bone, areas representing tissue (without bone present), areas representing background, areas representing collimation effects (e.g., areas of transition between x-ray intensity used for imaging, and areas that are collimated to reduce x-ray intensity and patient radiation dose), and areas corresponding to annotation markers (e.g., to indicate which hand is represented in a radiograph). In some embodiments, a user (e.g., a radiologist, a technician, etc.), can provide information indicating an area or areas of interest (e.g., regions of interest or ROIs) of a particular radiograph that correspond to one a particular type of object. In some such embodiments, each area can be labeled with the assistance of the user.

In some embodiments, the labeled regions of interest can be used to train a detection portion of an image preprocessing portion 412 of bone age assessment system 112. For example, as described below in connection with FIGS. 5 and 7, the regions of interest can be used to train a convolution neural network for identifying portions of a radiograph corresponding to a hand, and portions that do not correspond to a hand.

In some embodiments, radiograph images 404 can be preprocessed using preprocessing portion 412 to identify a hand region, and normalize the data included in the hand portion of each radiograph. In some embodiments, at 414, the preprocessed images can be used, with radiology reports 406, to generate training data to be used by a classification portion 416 of bone assessment system 104. As described below in connection with FIGS. 5, 8 and 9, in some embodiments, the training data generated at 414 can be used to train a convolution neural network included in classification portion 416 to classify a bone age represented in a received radiograph (e.g., of a left hand and wrist).

After training of bone age assessment system 104 during training phase 402, a radiograph 418 to be analyzed using bone age assessment system 104 can be received from any suitable source (e.g., an x-ray machine, an x-ray film scanner, a personal computer, a portable computer, a server, etc.). In some embodiments, as described below in connection with FIGS. 6 and 7, radiograph 418 can be preprocessed (e.g., by preprocessing portion 412), and used to determine a bone age represented in radiograph 418 (e.g., by providing the preprocessed radiograph to classification portion 416).

In some embodiments, classification portion 416 can optionally provide a range of potential bone ages that are represented in radiograph 418 at 420. For example, a most likely bone age determined by classification portion 416 can be presented with a range of other possible bone ages that are represented (e.g., two years less than the determined bone age, one year less than the determined age, one year more than the determined bone age, two years more than the determined bone age, etc.). In some embodiments, at 420, a user (e.g., a radiologist) can be presented with additional information to assist the user in determine which (if any) of the suggested bone ages are accurate. For example, the system can automatically present (or otherwise make available) information from an atlas corresponding to each bone age. As another example, the system can automatically present information about which feature(s) of the radiograph contributed most to the classification as a particular bone age (e.g., through an attention map).

At 424, an automatically determined (or semi-autonomously determined) bone age represented in radiograph 418 can be presented in connection with a processed image 426 of radiograph 418, and a structured radiology report 428 regarding the bone age assessment can be automatically generated. In some embodiments, such a report can be stored in connection with electronic medical records of the subject of radiograph 418, printed out and stored in a paper medical record, etc.

Figure 5:
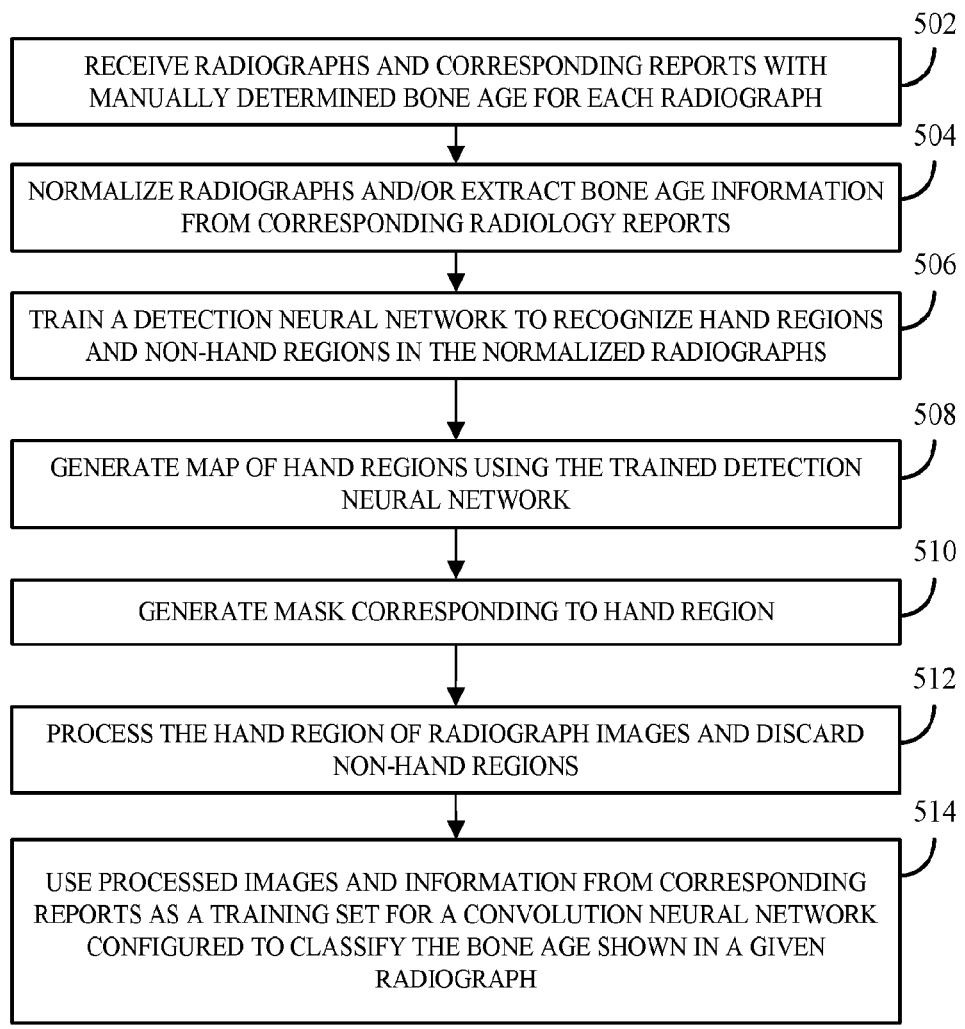
FIG. 5 shows an example of a process for training a bone age assessment system in accordance with some embodiments of the disclosed subject matter.

FIG. 5 shows an example 500 of a process for training a bone age assessment system in accordance with some embodiments of the disclosed subject matter. As shown in FIG. 5, at 502, process 500 can receive a set of radiographs and corresponding radiology reports with information about manually determined bone age represented in the radiograph. In some embodiments, the radiographs and corresponding radiology reports can be used to assemble a training dataset, a validation dataset, and/or a test dataset of corresponding pairs of radiographs and radiology reports. In some embodiments, as described above in connection with FIG. 4, process 500 can receive the set of radiographs at 502 from any suitable source, such as from electronic medical records, from paper medical records that have been digitized, from a corpus of bone age assessments and corresponding radiographs generated for the purpose of generating radiographs and radiology reports to be used to train a bone age assessment system.

At 504, process 500 can normalize radiographs received at 502 and/or can extract information about the bone age represented in the radiographs from the corresponding radiology reports. In some embodiments, process 500 can use any suitable technique or combination of techniques to normalize the radiographs. For example, the radiographs may not be stored with uniform formatting (e.g., greyscale base, intensity, contrast, size, etc.), and process 500 can normalize the formatting of the radiographs prior to using the radiographs for training the bone age assessment system. In a more particular example, as described below in connection with FIG. 11, some radiograph images received at 502 have black bones on white backgrounds, and others have white bones on black backgrounds. As another more particular example, image size may also vary considerably from thousands of pixels to a few hundred pixels. In some embodiments, to normalize the different grayscale bases, process 500 can determine the mean of pixels in a 10×10 patches in the four corners of each radiograph image, and can compare the means with a midpoint value in the brightness scale used by the image. For example, the patches can be compared to a brightness value of 128 for an 8-bit brightness resolution (i.e., a maximum brightness expressed in 8-bits is 256). Based on the comparison, process 500 can effectively determine whether a particular image has a white or black background. Based on the background color, process 500 can normalize the images to a consistent background color. For example, if a black background is going to be used to train the bone age assessment system, process 500 can convert each radiograph image determined to have a white background to an image having a black background, or vice versa. In some embodiments, process 500 can use any suitable technique or combination of techniques to convert radiograph images with, for example, a white background to an image with a black background. For example, process 500 can invert the brightness value of each pixel, such that a value of 256 becomes a brightness of 0, a brightness of 127 becomes a brightness of 129, etc. Note that using a larger brightness resolution (e.g., 14-bit or 16-bit) may facilitate more accurate results, as there is more information available given the same sized image due to finer gradations in brightness.

In some embodiments, process 500 can normalize the size of the radiograph images received at 502 using any suitable technique or combination of techniques. For example, as most hand radiographs are heightwise rectangles, process 500 can convert the spatial resolution of each radiograph image to have the same heights in pixels, and a width in pixels that maintains substantially the same aspect ratio of the original radiograph image. In a more particular example, each radiograph can be converted to have a height of 512 pixels, and through zero padding to fill out the width (as most radiographs have larger heights than widths) to 512 pixels. That is, process 500 can normalize each radiograph image to have a size of 512×512 pixels. Note that this is merely an example, and other sizes can be used when normalizing radiographs to be used in training. For example, a neural network may require a minimum size (e.g., 224× 224 pixels), and using images of this size can decrease the time required to train the neural network, and can decrease the time required to perform an automated bone age assessment. However, this can also result in a less accurate system due the relative dearth of information contained in the smaller sized images. By contrast, using larger image sizes may result in a more accurate analysis, but may require an unacceptable long time to train and/or generate results.

At 506, process 500 can use information from at least a portion of the normalized radiograph images to train a detection system for classifying different portions of the image as corresponding to different types of objects included in the radiograph images. For example, as described above in connection with 410 of FIG. 4, a typical radiograph of a hand may include various different types of objects, such as, bone, tissue, background, collimation, and annotation markers In some embodiments, process 500 can use any suitable technique or combination of techniques to train such a detection system. For example, process 500 can train a convolution neural network to detect bones and tissues.

In some embodiments, process 500 can receive information identifying image patches corresponding to the different classes of objects from the normalized images through manually (and/or human assisted) selected regions of interest (ROIs). For example, a human (or humans) can identify various patches in a particular radiograph (or radiographs) that primarily correspond to each of the classes of object. As another example, a human (or humans) can different which portions of a radiograph correspond to bone, tissue, etc., by drawing borders representing the edges between different classes of objects. In a more particular example, as described below in connection with FIG. 7, process 500 can receive a set of image patches representing a balanced dataset with 100K samples from each class taken from at least a portion of radiograph images received at 502. In such an example, the 100K samples can be from 300 unique radiographs.

In some embodiments, process 500 can train any suitable type of neural network to detect different classes of objects in radiograph images. For example, process 500 can train a convolution neural network to detect such objects. In a more particular example, a convolution neural network based on the LeNet-5 network topology can be used, as it is a relatively efficient model for coarse-grained recognition of obviously-distinctive datasets, and has been successfully used in applications such as MNIST digit recognition. (See for example, Yann Lecun, et al., "Gradient-based Learning applied to Document Recognition," Proceedings of the IEEE, Vol. 86, pp. 2278-2324, November 1998), which is hereby incorporated by reference herein in its entirety, and Yann Lecun et al., "The MNIST Database of Handwritten Digits," available at http(colon)//yann(dot)lecun(dot)com/exdb/mnist/). In such a more particular example, the network topology of LeNet-5 can be modified by using a smaller input size (e.g., 24×24) and by changing the number of outputs for the SoftMax classifier to five classes (i.e., one for each class expected to be in the radiograph images).

At 508, process 500 can use the trained detection system (e.g., a trained detection CNN) to generate map hand regions in each normalized radiograph, using any suitable technique or combination of techniques to create hand mapping information. In some embodiments, process 500 can assign a particular class (e.g., bone, tissue, background, etc.) to each pixel in a normalized radiograph based on the output(s) of the image data with the trained detection system. For example, as described below in connection with FIGS. 7 and 12, the trained detection system can be used to classify 24×24 patches from the image as belonging to a particular class for each 24×24 patch in the image. In a more particular example, process 500 can sample patches of 24×24 pixels across the entire image (e.g., by using a first 24×24 patch from the top-left corner of the image, moving any suitable number of rows to the right and using a second 24×24 patch, moving back to the left edge and down a suitable number of rows when a 24×24 path including each column has been used, etc.). In such a more particular example, the detection system can generate a score for each patch indicating the likelihood that the patch corresponds to each class of object, and process 500 can record, for each pixel in the patch, the score from analyzing a particular patch including that pixel. Process 500 can then assign a particular class to each pixel based on the scores. In some embodiments, any suitable stride length (i.e., the number of pixels the patch is moved between samples), resulting in any suitable amount of overlap between patches can be used when determining per pixel scores. For example, a stride length of 24 can be used, which results in no overlap between samples, and a single score associated with each pixel. As another example, a stride length of one can be used, which results in multiple scores being assigned to some pixels, especially in the center. In such an example, the classification of each pixel can be based on the total scores associated with that pixel determined from all patches that included the pixel. As the top-left corner pixel is included in only a single patch, that pixel would be classified based on the results of analyzing that one patch, while a pixel in the center of the image would be included in dozens of patches. Any other suitable stride length can be used, where a shorter stride length results in more computations being carried out, but may result in a more accurate and/or higher resolution labeling. Whereas a larger stride length requires less calculation, but may result in a less accurate and/or lower resolution labeling.

At 510, process 500 can generate a mask corresponding to a portion of a radiograph for an area determined to be most likely to correspond to a hand using any suitable technique or combination of techniques. In some embodiments, process 500 can include pixels identified as corresponding to hand (i.e., bone or tissue) by the detection system in the mask that are likely to correspond to a portion of the hand, and not include portions that are likely to be false positives. For example, in some embodiments, process 500 can identify a largest contiguous area that is labeled as being hand pixels, and can discard hand pixels that are not contiguous. Additionally, in some embodiments, process 500 can assign non-hand pixels that are surrounded by the contiguous area (or bounded by the contiguous area and an edge of the radiograph image) to mask.

At 512, process 500 can use one or more image processing techniques on the radiograph images to produce images more suitable for classification (e.g., by a classification CNN) using any suitable technique or combination of techniques. For example, process 500 can use the mask to remove information from the image that does not correspond to the hand that is the subject of the radiograph. In a more particular example, pixels that do not correspond to the mask can be set to a brightness value corresponding to no occlusion of the radiation used to create the radiograph (e.g., zero for black background, or a maximum value, such as 256 for an image encoded using an 8-bit brightness resolution). In another more particular example, the portions corresponding to the mask can be copied to a new image (e.g., by cropping all pixels not corresponding to the mask). As another example, process 500 can center the portion corresponding to the mask within the image, which can reduce translational variance between images which may adversely affect the accuracy of a convolution neural network being trained with such information and/or from properly classifying an image submitted to the neural network for classification. In a more particular example, the pixels corresponding to the mask can be centered in a 512×512 pixel image with zero padding to fill in portions not corresponding to the mask. As yet another example, process 500 can enhance contrast in the image between bone and tissue or background. In a more particular example, process 500 can use one or more histogram equalization techniques to enhance contrast in the image. As still another example, process 500 can any other suitable techniques, such as techniques to reduce noise in the image (e.g., by using one or more denoising techniques), sharpen lines in the image (e.g., using one or more sharpening filters), etc., which can enhance visibility of the bones for learning and/or analysis by a convolution neural network.

In some embodiments, process 500 can apply image processing techniques in a particular order that enhances the visibility of bones in the radiograph to a greater extent than would be provided by another order. For example, process 500 can remove artifacts from the image, center the remaining image data (e.g., in a new 512×512 image, with zero padding for regions outside the mask region), perform contrast enhancement on the centered image data, denoise the contrast enhanced image data, and apply an edge sharpening filter to the denoised image data.

At 514, process 500 can train a convolution neural network using the processed radiograph images and corresponding radiology reports using any suitable technique or combination of techniques. In some embodiments, process 500 can use the processed radiograph images to train a deep convolution neural network that include alternating convolution and pooling layers to learn layered hierarchical and representative abstractions from input images, followed by fully-connected classification layers which are trainable with feature vectors extracted from earlier layers. In general, manual bone age assessment is generally determined based on progression in epiphyseal width relative to the metaphyses at different phalanges, carpal bone appearance, and radial or ulnar epiphyseal fusion, but not by the shape of the hand and wrist. In general, sub-category recognition tasks are more challenging in comparison to basic level recognition, as less data and fewer discriminative features are available. In some embodiments, accuracy of fine-grained recognition can be made by using transfer learning techniques. In such embodiments, low-level knowledge from a large-scale dataset can be leveraged, and the weights can be fine-tuned to make the previously trained neural network specific for a target application. Although medical images are different from natural images, transfer learning can be used to adapt generic filter banks trained on large datasets (e.g., the ImageNet dataset), and parameters can be adjusted to render high-level features specific for medical applications.

In some embodiments, process 500 can use any suitable trained image recognition deep CNN such as AlexNet (e.g., as described in Alex Krizhevsky, et al., "Imagenet Classification with Deep Convolutional Neural Networks," Advances in Neural Information Processing Systems, 2012, pp. 1097-1105.), GoogLeNet (e.g., as described in Christian Szegedy, et al. "Going Deeper with Convolutions," 2015 IEEE Conference on Computer Vision and Pattern Recognition (CVPR), 2015), or VGG-16 (e.g., as described in Karen Simonyan, et al., "Very Deep Convolutional Networks for Large-Scale Image Recognition," arXiv(dot)org, 2014), which were validated in the ImageNet Large Scale Visual Recognition Competition (ILSVRC). As shown below in TABLE 2, these various deep CNNs use different numbers of trainable parameters, different amounts of computing resources, and varying performance.

TABLE 2

| | # of trainable parameters | # of operations at inference time | Single-crop top-1 validation accuracy |
|---|---|---|---|
| GoogLeNet | ~5 M | ~3 Gflops | ~68% |
| AlexNet | ~60 M | ~2.5 Gflops | ~54.5% |
| VGG-16 | ~140 M | ~32 Gflops | ~70.6% |

As shown in TABLE 2, there can be a tradeoff between accuracy and computational resource intensity. For example, if accuracy is the sole determiner, VGG-16 is the best performer and AlexNet is the worst. However, when taking the amount of computing resources into account (which can correlate with the amount time required to train and/or use the neural network), GoogLeNet utilizes ~25 times fewer trainable parameters to achieve comparable performance to VGG-16 with a faster inference time. Additionally, GoogLeNet is the most efficient neural network, as the inception modules described below in connection with in FIG. 9, can facilitate greater capability to learn hierarchical representative features without using as many trainable parameters by reducing the number of fully-connected layers.

In some embodiments, process 500 can use a modified version of an already trained image recognition deep CNN, such as GoogLeNet. For example, process 500 can use a version of GoogLeNet with the first layer filters, which ordinarily correspond to three color channels (e.g., R, G, and B), replaced with a single channel representing grayscale values of image radiographs. In such an example, the three color channels can be converted to a single channel by taking the arithmetic mean of the preexisting RGB values.

In some embodiments, after initializing the convolution neural network with the pre-trained model, process 500 can further train the convolution neural network using any suitable combination of parameters and techniques. For example, process 500 can use a stochastic gradient descent optimizer with a mini-batch size of 96 using any suitable combination of hyperparameters, any suitable base learning rates (e.g., 0.001, 0.005, 0.01, etc.), any suitable weight decay (e.g., 0.001, 0.005, 0.01), any suitable gamma values (e.g., 0.1, 0.5, 0.75, etc.), with any suitable momentum term (e.g., 0.9).

In some embodiments, process 500 can use any suitable technique or combination of techniques to reduce the likelihood that the trained neural network will be overfitted to the training data set. In general, deep neural networks require a large amount of labeled training data for stable convergence and high classification accuracy, whereas limited training data may cause deep neural networks to overfit and fail to generalize for a target application. This can be particularly challenging in medical imaging, as compilation of high quality and well-annotated images is typically a laborious and expensive process. Accordingly, process 500 can use one or more techniques to decrease the risk of overfitting. For example, process 500 can use one or more data augmentation techniques to synthetically increase the size of the training dataset with geometric transformations, pixel transformations, noise injections, and/or color jittering, while preserving the same image label. In some embodiments, techniques such as those shown below in TABLE 3 can be used, such as geometric, contrast, and brightness transformations used for real-time data augmentation. Affine transformations, including rotation, scaling, shearing, and pixel variation can also be utilized to improve resiliency of the network to geometric variants, and variations in contrast or intensity of an input image. In some embodiments, transformations can be augmented with random switches for each transformation. Using such real-time data augmentation, a single image can be transformed into one of 110, 715,000 possible images (i.e., 61*150*121*100), which can reduce the likelihood of image repetition during each training epoch. In some embodiments, such transformations and/or other augmentations can be performed without increasing computing time or storage as images for the next iteration are augmented on a CPU while the previous iteration of images are being used to train the CNN using a GPU. Other transformations that may be used for natural images (e.g., horizontal inversion or random translation) can be less useful as bone age assessment is typically done on radiographs of a patients left hand and/or writs by convention, and the images are centered during preprocessing.

TABLE 3

| Technique | Range | # of Synthetic Images |
|---|---|---|
| Rotate | −30° ≤ rotation angle ≤ 30° | 61 |
| Resize | 0.85 ≤ width ≤ 1.0, 0.9 ≤ height ≤ 1.0 | 150 |
| Shear | −5° ≤ angle ≤ 5°, −5° ≤ y angle <5° | 121 |
| Pixel Transform | α * pixel + β, (0.9 ≤ α ≤ 1.0, 0 ≤ β ≤ 10) | 100 |

In some embodiments, the convolution neural network can be validated and/or otherwise tested (e.g., using a portion of radiographs received at 502 that were reserved for such a purpose) after each training epoch, and upon reaching a satisfactory performance and/or after performance has not increased for a particular number of epochs (e.g., to prevent overfitting).

In some embodiments, process 500 can be executed by one or more computing devices used to train the bone age assessment system, and the trained system can be distributed to one or more other computing devices for performing bone age assessments. For example, process 500 can be executed at a server, and the trained bone age assessment system can be executed by a computing device, such as a personal computer, a laptop computer, a smartphone, a tablet computer, etc., that is local to a user of the bone age assessment system (e.g., a radiologist).

Figure 6:
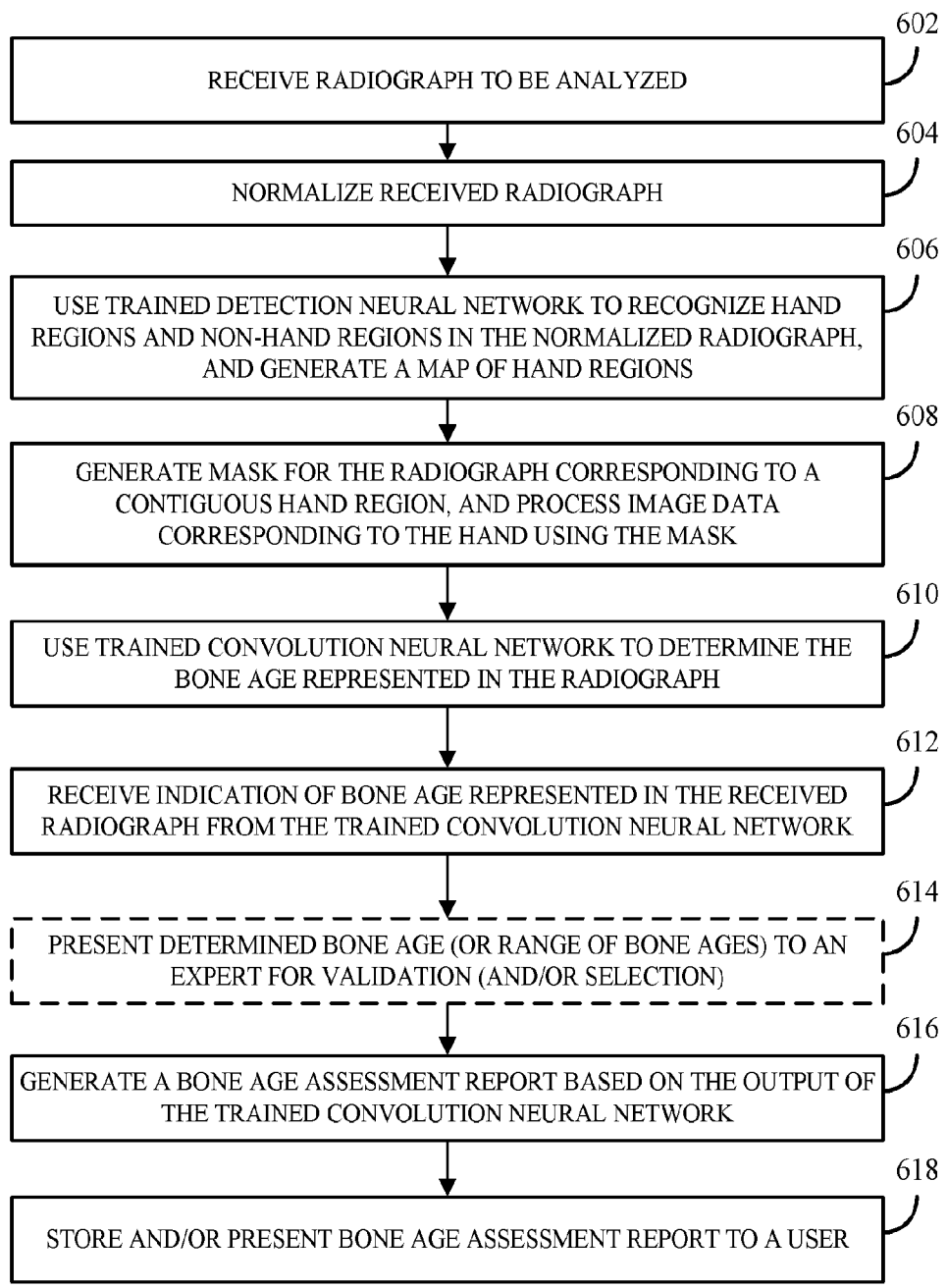
FIG. 6 shows an example of a process for performing an automated bone age assessment in accordance with some embodiments of the disclosed subject matter.

FIG. 6 shows an example 600 of a process for performing an automated bone age assessment in accordance with some embodiments of the disclosed subject matter. As shown in FIG. 6, at 602, process 600 can receive a radiograph to be analyzed by a trained bone age assessment system. As described above in connection with FIG. 4, the radiograph can be received from any suitable source, at any suitable computing device.

At 604, process 600 can normalize the received radiograph using any suitable technique or combination of techniques, such as techniques described above in connection with 504 of FIG. 5.

At 606, process 600 can use a trained detection neural network (e.g., the detection CNN trained at 506 as described above in connection with FIG. 5) generate a map or hand regions in the received radiograph (e.g., as described above in connection with 508 of FIG. 5).

At 608, process 600 can generate a mask corresponding to a hand represented in the received radiograph image using any suitable technique or combination of techniques, such as techniques described above in connection with 510 of FIG. 5. Additionally, in some embodiments, process 600 can perform any suitable image processing on the radiograph image received at 602, such as by using image processing techniques described above in connection with 512.

At 610, process 600 can use a trained convolution neural network, such as the network described above in connection with 514 of FIG. 5, to determine a bone age represented in the radiograph received at 602. In some embodiments, the radiograph image submitted to the trained convolution neural network can be an image that has been processed as described above in connection with 604-608.

At 612, process 600 can receive an indication of the bone age represented in the received radiograph from the trained convolution neural network. As described above in connection with FIG. 4, the trained convolution neural network can provide an indication of bone age, and in some embodiments, a confidence in the assessment of the bone age. Additionally, in some embodiments, at 612, process 600 can receive information indicative of which area(s) contributed most to the convolution neural network classification of the radiograph image as corresponding to the output bone age (e.g., information that can be used to create an attention map).

At 614, process 600 can (optionally) present the determined bone age (or a range of bone ages, based on uncertainty of the assessment) to an expert for validation and/or selection of a particular bone age to assign to the radiograph image. As described above in connection with 422 of FIG. 4, process 600 can cause one or more images based on the received radiograph image to be presented to the expert, and can make available (or present) portions of an atlas corresponding to the determined bone age to aid the expert in validating, and/or selecting from among, the bone age(s) determined by the convolution neural network. Additionally, in some embodiments, process 600 can use attention information to bring the experts attention to portions of the radiograph that were particularly relevant to the convolution neural networks' assessment (e.g., by highlighting areas, by zooming in on areas, etc.).

At 616, process 600 can generate a bone age assessment report based on the output of the trained convolution neural network. In some embodiments, the bone age assessment report can include any suitable information or combinations of information, such as the radiograph image as received, the processed radiograph image, an output from the convolution neural network, identifying information (e.g., the name) of an expert (e.g., a radiologist) that reviewed the assessment, an indication of whether the expert validated the output of the convolution neural network or selected a different bone age, information provided by the expert indicating why another bone age was selected, attention map information, etc.

At 618, process 600 can store the generated bone age assessment for later use and/or comparison, and/or can present the bone age assessment report to a user (e.g., a primary doctor or other specialist treating the subject of the radiograph image). For example, in some embodiments, process 600 can store the bone age assessment in an electronic medical record system in connection with medical records corresponding to the subject of the radiograph image received at 602.

Figure 7:
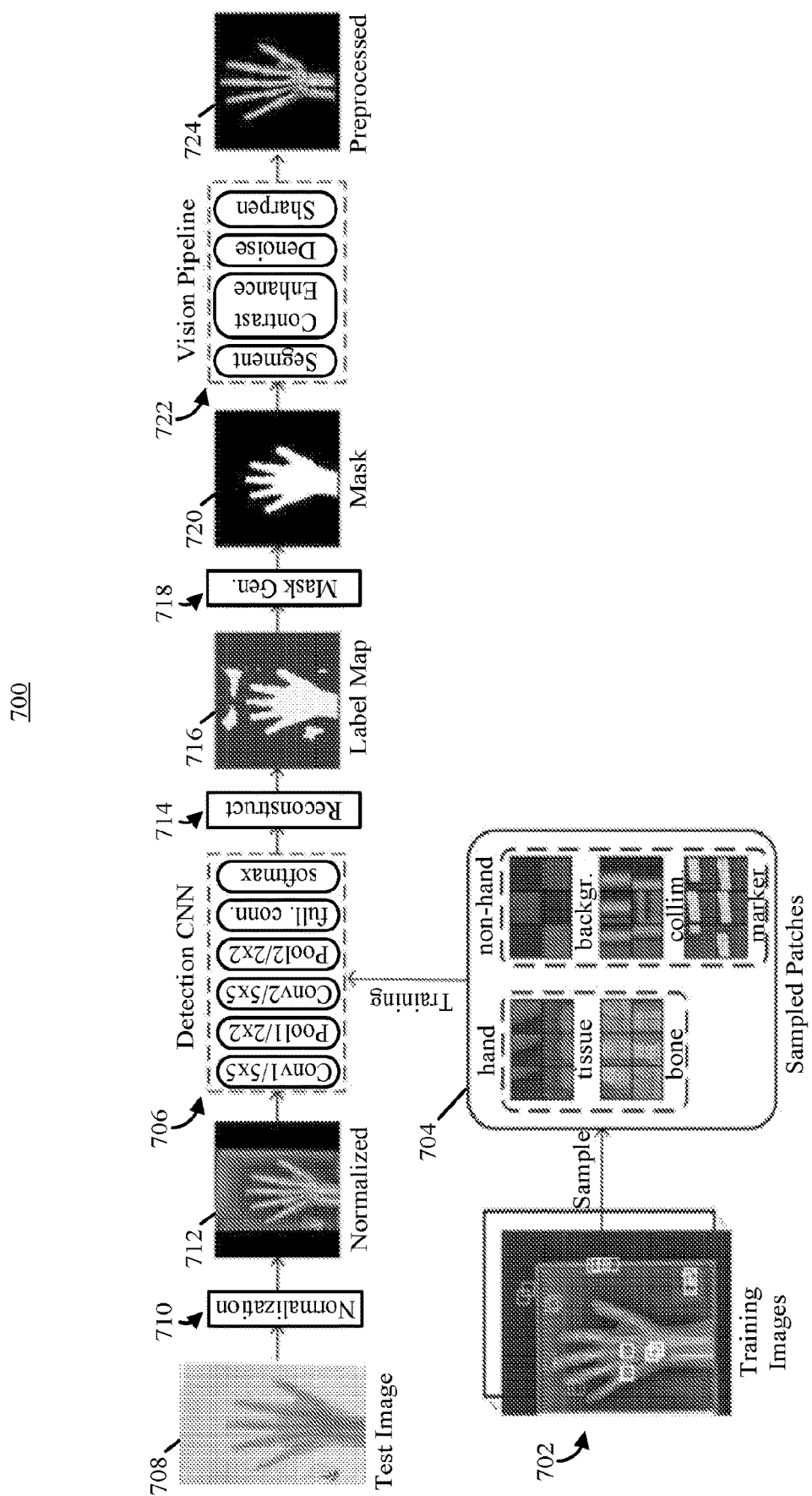
FIG. 7 shows an example of a flow for training and using mechanisms for preprocessing radiograph images in accordance with some embodiments of the disclosed subject matter.

FIG. 7 shows an example 700 of a flow for training and using mechanisms for preprocessing radiograph images in accordance with some embodiments of the disclosed subject matter. As shown in FIG. 7, training images (e.g., that have been normalized as described above in connection with 504 of FIG. 5) can be used as a source of sample patches 704 corresponding to different types of objects included in radiographs used in bone age analysis (e.g., as described above in connection with 410 of FIG. 4). As described above in connection with 412 of FIGS. 4 and 506 of FIG. 5, the samples can be used to train a detection convolution neural network 706 that can be used to label pixels in a received test image 708 as belong to a hand region, or a non-hand region. In some embodiments, detection convolution neural network 706 can be any suitable neural network that can be used to classify portions of an image as likely belonging to a particular class. For example, as shown in FIG. 7, detection convolution neural network 706 can be a convolution neural network with two convolution layers (i.e., conv1 using a 5×5 kernel, and conv2 using a 5×5 kernal), two pool layers (i.e., pool1 using a 2×2 filter, and pool2 using a 2×2 filter), one fully connected layer, and a softmax output layer that calculates a normalized class probability for each of the classes of objects provided in the training patches. In some embodiments, any suitable pooling function can be used in each of the various pooling layers, such as max pooling, average (mean) pooling, L2 norm pooling, etc.

In some embodiments, at 714, a reconstruction operation is performed to generate a map for labeling pixels of normalized radiograph 712 as being hand pixels, or non-hand pixels (e.g., as described above in connection with 508 of FIG. 5). As described above in connection with 508 of FIG. 5, concurrent patches of normalized radiograph 712 can be provided to detection convolution neural network 706, which can provide a probability that the patch corresponds to each class, and a score can be calculated for each pixel based on the cumulative scores for that pixel as part of each patch that was analyzed by detection convolution neural network 706. Based on the score, at 714, each pixel can be assigned as corresponding to a hand region, or not corresponding to a hand region, to create a label map (e.g., as represented by label map 716). In some embodiments, a mask 718 corresponding to a hand region test image 708 can be generated based on the label information (e.g., as described above in connection with 510 of FIG. 5).

In some embodiments, mask 720 and normalized radiograph 712 can be used by a image processing pipeline (e.g., vision pipeline 722) to generate a processed radiograph 724 that can be used as an input into a classification convolution neural network. Note that flow 700 can be used to process training images (e.g., training images 702) used to train the classification convolution neural network, as well as test images that are to be classified by the classification convolution neural network.

Figure 8:
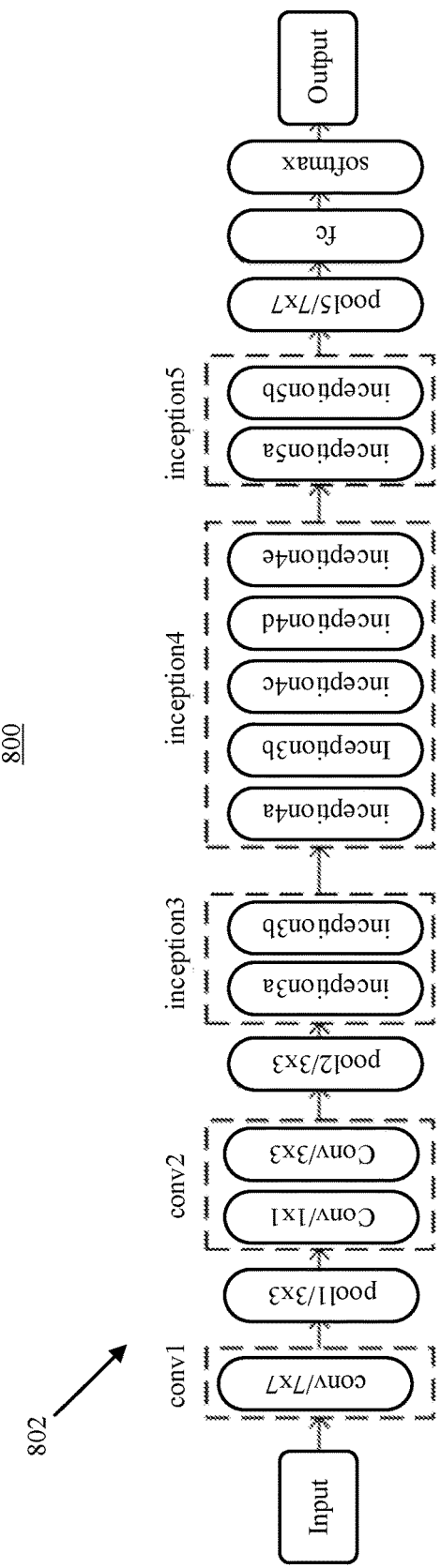
FIG. 8 shows an example of a topology of convolution neural network that can be trained and used to classify bone age represented in a radiograph in accordance with some embodiments of the disclosed subject matter.

FIG. 8 shows an example 800 of a topology of convolution neural network 802 that can be trained and used to classify bone age represented in a radiograph in accordance with some embodiments of the disclosed subject matter. In some embodiments, convolution neural network 802 can have a similar topology to a convolution neural network described in Szegedy, et al. "Going Deeper with Convolutions."

Figure 9:
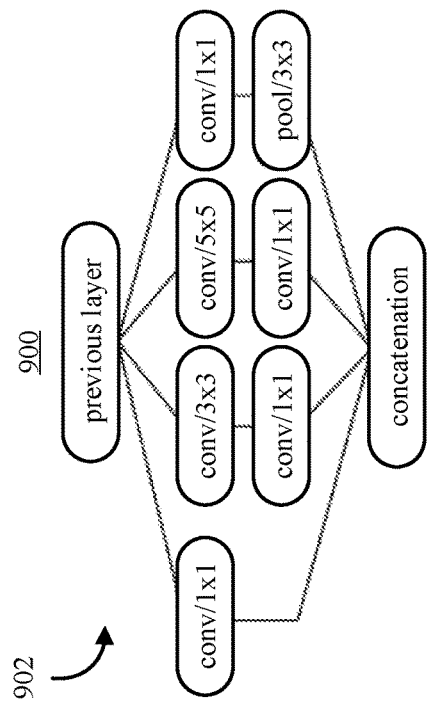
FIG. 9 shows an example of an inception module used in convolution neural network in accordance with some embodiments of the disclosed subject matter.

FIG. 9 shows an example 900 of an inception module 902 used in convolution neural network 802 in accordance with some embodiments of the disclosed subject matter. In some embodiments, inception module 902 can have a similar topology to an inception module described in Szegedy, et al. "Going Deeper with Convolutions."

Figure 10:
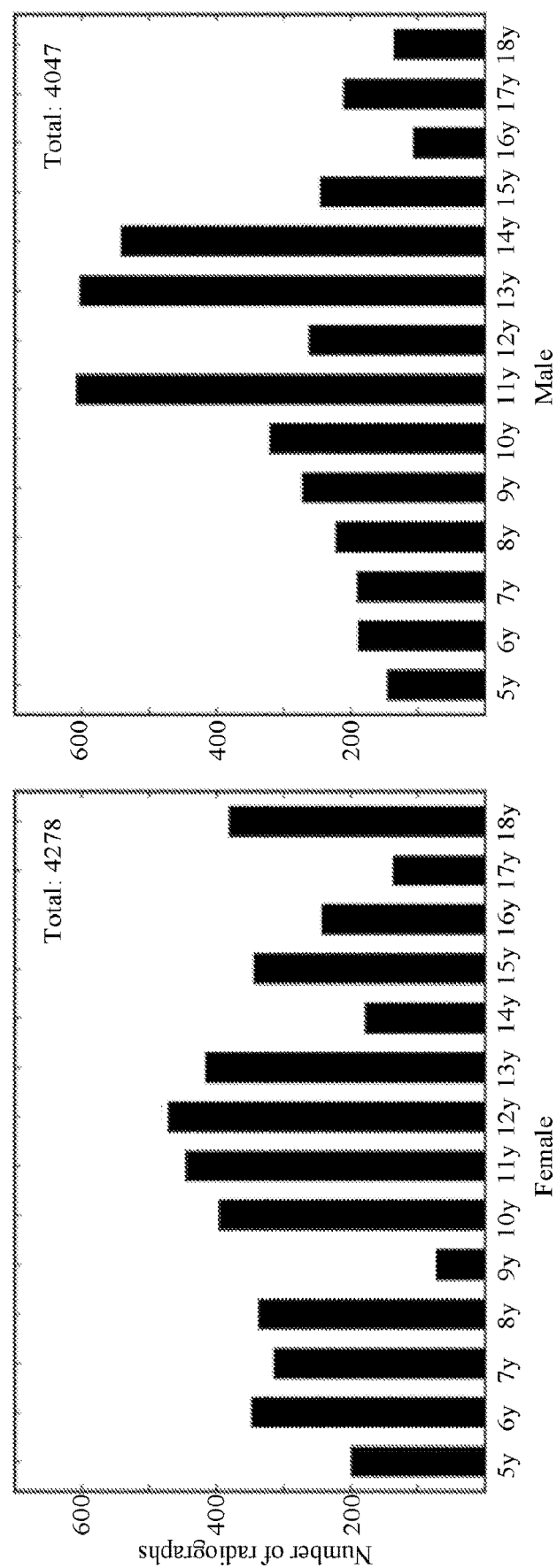
FIG. 10 shows an example of samples of radiographs and corresponding radiology reports used in an example implementation of some mechanisms described herein in accordance with the disclosed subject matter.

FIG. 10 shows an example 1000 of samples of radiographs and corresponding radiology reports used in an example implementation of some mechanisms described herein in accordance with the disclosed subject matter. As shown in FIG. 10, radiographs and corresponding radiology reports for male and female patients with chronological age of 5-18 years and skeletally mature (18 years and up) were included in a training dataset. The reports were collected by searching medical records (with approval from the Internal Review Board) using an internal report search engine to identify radiographs and radiology reports using the exam code "XRBAGE" that were generated from 2005-2015. Images formatted using the Digital Imaging and Communications in Medicine (DICOM) format corresponding to the radiographs were also collected. The radiology reports included the patient's chronological age, and the bone age determined by the radiologist with reference to the standards of Greulich and Pyle, 2nd edition Note that samples from patients with chronological ages from zero to four years were excluded due to limited availability, and because the overwhelming indication for bone age assessment for the patients was for delayed puberty, short stature, or precocious puberty. This generally excludes patients of age four or less, as bone age assessment examinations for such issues are infrequently performed for patients less than 5 years of age. Reported bone ages were extracted from the radiologist reports using bone age-related keywords such as "bone age" and "skeletal." The extracted bone ages were defined in years, floored (i.e., rounded down to the nearest year), and categorized by year ranging from 5-18 years. Skeletally mature cases were considered to have a bone age of 18 years. For cases where the reported bone ages in the radiology reports were given as a range, the arithmetic mean of the range was used as the actual bone age. After excluding aberrant cases, such as right hands, deformed images, and uninterpretable reports, radiographs were labeled by skeletal age and gender as shown in FIG. 10. Of the remaining radiographs with assigned ages, 15% were randomly selected to be part of a validation dataset, 15% were randomly selected to be used as a test dataset, and the remainder (70%) were used as training datasets for the female and male cohorts, with separate neural networks (e.g., with the same network topology) trained for the female and male cohorts. The validation data was utilized to tune hyperparameters and perform early stopping to find the best model out of several trained models during each epoch of training of the classification convolution neural network. Different convolution neural networks were evaluated using the test datasets to determine whether the top-1 prediction (i.e., the bone age determined by the classification neural network as being most likely to be represented in the radiograph) matched the ground truth (i.e., the bone age determined based on the radiology report, which was subjectively determined by a radiologist), was within 1 year of the ground truth, was within 2 years of the ground truth, or was not within 2 years of the ground truth. In order to make a fair comparison between different networks, the same split datasets were used to train and test each network as new random datasets might affect the accuracy as compared to using the dataset used for another network.

Figure 11:
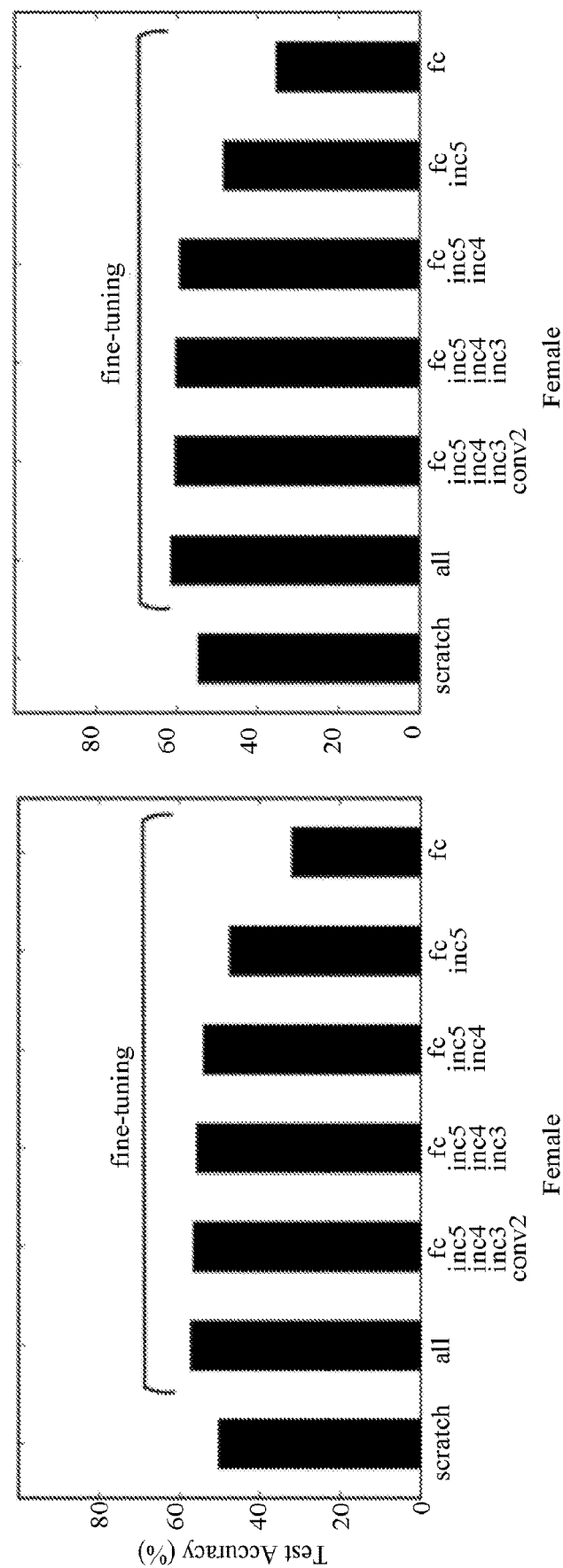
FIG. 11 shows examples of resultant accuracy achieved using different approaches for training the classification convolution neural network in accordance with some embodiments.

FIG. 11 shows examples 1100 of resultant accuracy achieved using different approaches for training the classification convolution neural network in accordance with some embodiments. In general, layer-wise fine-tuning schema can provide better performance for a given application with a limited amount of training data than training a convolution neural network using only that limited data (i.e., training the network from scratch, not starting with an already trained network). For example, early layers can learn low-level image features, like edges and corners, while the later layers can be tuned to learn higher-level features applicable for the target application. Transfer learning typically includes fine-tuning the later layers to the specific dataset, but it may also involve fine-tuning early layers, depending on how different the data that was used to initially train the network is from the target application. To find the optimal number of layers requiring adjustment for bone age analysis using the mechanisms described herein, a regressive test was conducted by incrementally fine-tuning pre-trained convolution neural networks from the last layer to the first. In addition, the convolution neural network was trained from scratch with a random weight initialization to determine whether fine-tuning was better than training from scratch. A grid search for finding the optimal combination of hyperparameters, as described below, was conducted to ensure the final accuracy for each test was optimal. FIG. 11 presents test accuracy for the combination of hyperparameters tested that produced the most accurate results, with the real-time data augmentation, for the pre-trained convolution neural networks that were fine-tuned for layers ranging from fully-connected (fc) to all layers. A base learning rate of 0.005 was used for the best performing models at fine-tuning tests and a base learning rate of 0.01 was employed for training from scratch. If relatively large learning rates are used for fine-tuning the pre-trained model, well-trained generic features may be overwritten, causing overfitting of the model. As shown in FIG. 11, in this example, fine-tuning weights of all layers was found to be the best scheme for bone age analysis. Since medical images are markedly different from natural images on which most networks were originally trained, fine-tuning all layers to generate low-level and high-level features for bone age analysis can increase the accuracy of the fine-tuned convolution neural network. When training the network from scratch using only medical images, there were many cases where the loss function failed to converge, implying that random weight initialization is not a stable training technique given the small amount of data available for training.

After initializing a convolution neural network with a pre-trained model, each of the networks was further trained using a stochastic gradient descent optimizer with a mini-batch size of 96 using 27 different combinations of hyper-parameters, including base learning rates [0.001, 0.005, 0.01], weight decays [0.001, 0.005, 0.01], and gamma values [0.1, 0.5, 0.75], in conjunction with a momentum term of 0.9. An extensive grid search was performed on an NVIDIA® DevBox, containing four Titan X GPUs with 7 TFlops of single-precision floating point accuracy, 336.5 GB/s memory bandwidth, and 12 GB RAM per GPU. After finding the combination of the utilized hyperparameters that performed best on the validation dataset, the best model was selected and evaluated using the test dataset. Each training experiment was stopped when the validation accuracy plateaued, and all experiments were completed prior to 100 epochs.

The detection convolution neural network modified as described above in connection with FIG. 5 (e.g., using a smaller input size of 24×24, and modifying the softmax layer to provide five outputs) requires relatively small amounts of computations and trivial memory space for trainable parameters at deployment time. An example of the detection convolution neural network was trained with the set of the sampled patches (e.g., the 100K patches extracted from 300 unique radiographs for 100 epochs using a stochastic gradient descent algorithm with 0.01 of the base learning rate decreased by three steps based on convergence to loss function. In the testing, 25% of images per class were held out as a validation dataset to select the best model out of epochs. The best trained detection network achieved 99.2% of validation accuracy to classify an object for a given patch.

Figure 12:
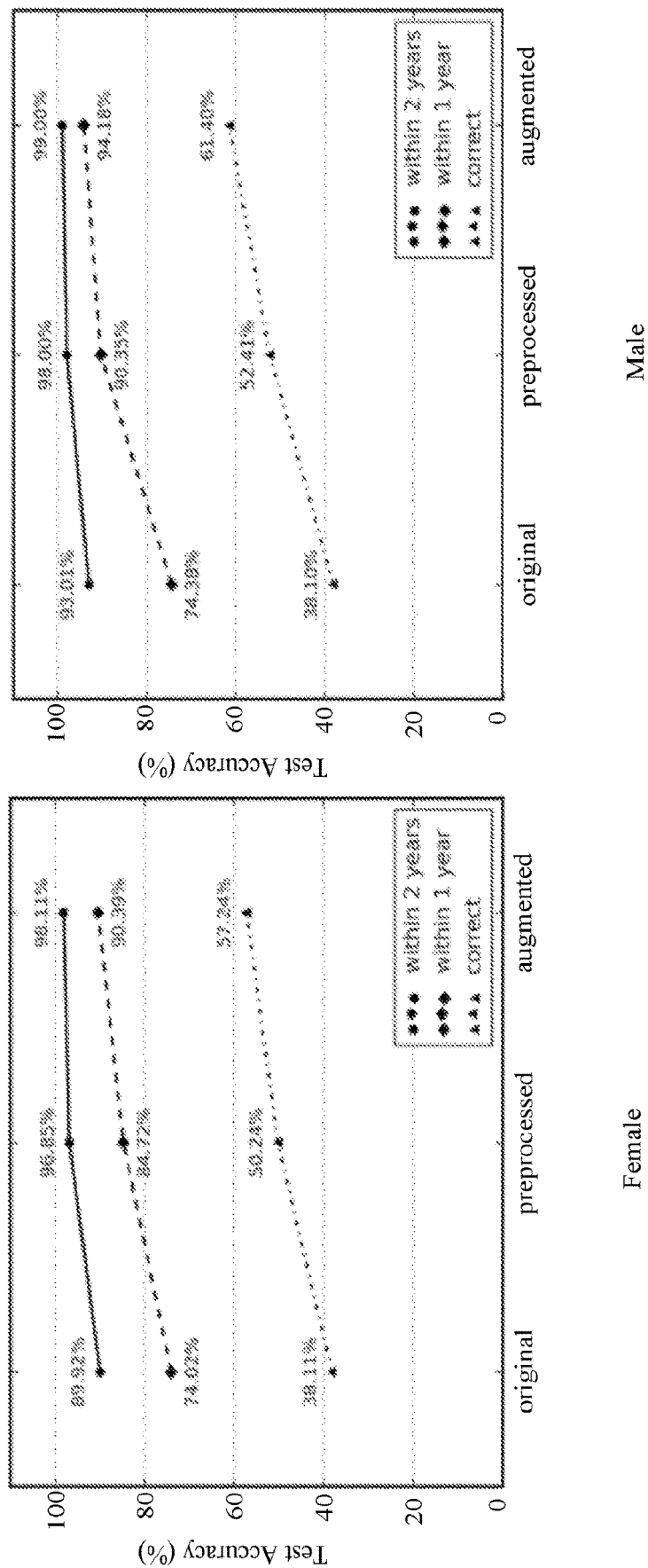
FIG. 12 shows examples of accuracies of a classification convolution neural networks trained using various types of training datasets in accordance with some embodiments of the disclosed subject matter.

FIG. 12 shows examples 1200 of accuracies of a classification convolution neural networks trained using various types of training datasets in accordance with some embodiments of the disclosed subject matter. As shown, generically trained convolution neural networks were fine-tuned (e.g., as described above in connection with FIG. 11 using original radiographs that were converted to 224×224 pixels in size, using preprocessed images (e.g., as described above in connection with FIG. 7), and using preprocessed images with real-time image augmentation (e.g., as described above in connection with TABLE 3). As shown in FIG. 12, accuracy was 38.11% for the female cohort and 38.10% for the male cohort using original (unprocessed) radiographs, were assigned an age within 1 year of ground truth 74.02% and 74.38% of the time, respectively, and within 2 years 89.92% and 93.01% of the time, respectively. Using preprocessed images, accuracy improved to 50.24% for the female cohort and 52.41% for the male cohort, while accuracy within 1 year (84.72%, 90.35%) and 2 years (96.85%, 98.00%) also improved. Using preprocessed images that were augmented during training accuracy improved to 57.24% for the female cohort and 61.40% for the male cohort, while accuracy within 1 year (90.39%, 94.18%) and 2 years (98.11%, 99.00%) also improved. Using the augmented images, Root Mean Squared Error (RMSE) was 0.93 years for females and 0.82 years for males, decreasing by 58% for the female and 56% for the male cohorts compared to RMSE for original images.

Figure 13:
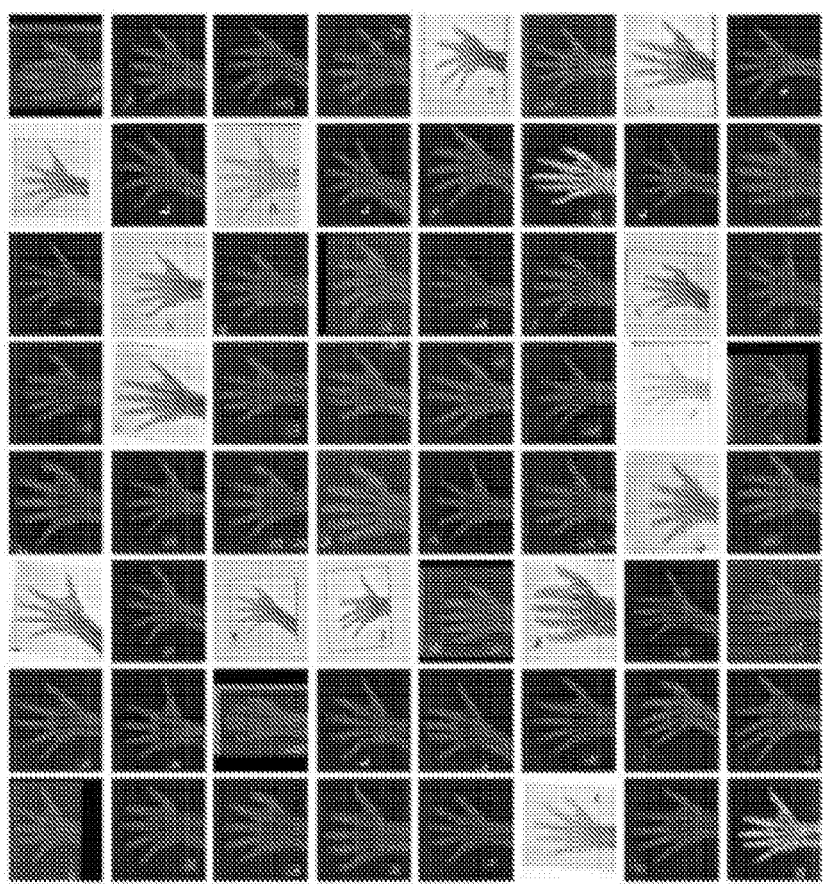
FIG. 13 shows examples of various different original radiographs used in training and/or testing the detection and/or classification convolution neural networks in accordance with some embodiments of the disclosed subject matter.

FIG. 13 shows examples of various different original radiographs used in training and/or testing the detection and/or classification convolution neural networks in accordance with some embodiments of the disclosed subject matter. As shown in FIG. 13, where radiographs of various sizes were converted to a relatively uniform size for easier comparison, the characteristics and quality of radiographs can be vary significantly.

Figure 14:
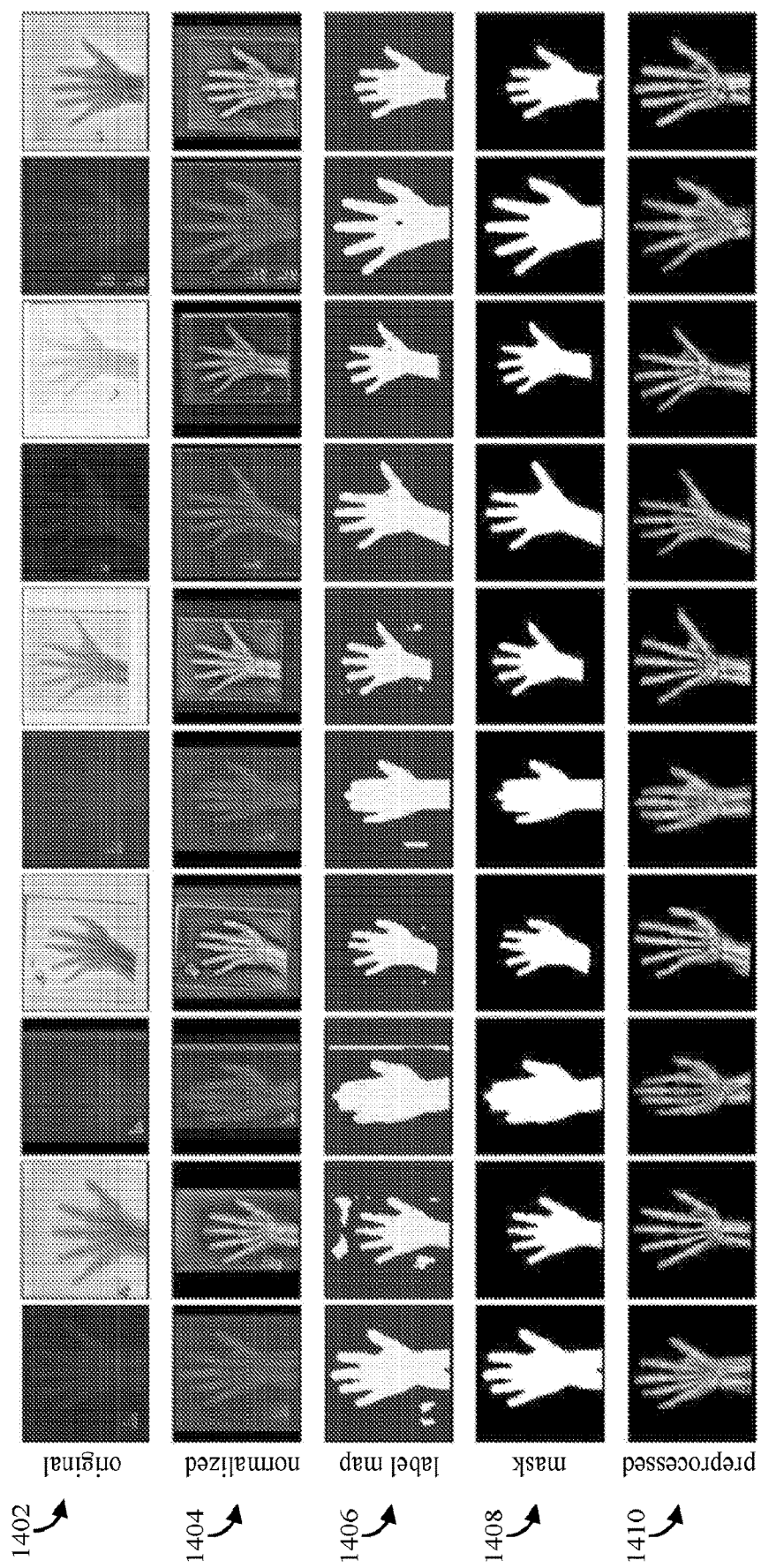
FIG. 14 shows examples of the results of preprocessing various input radiographs in accordance with some embodiments of the disclosed subject matter.

FIG. 14 shows examples of the results of preprocessing various input radiographs in accordance with some embodiments of the disclosed subject matter. As shown in FIG. 14, various original images 1402 were normalized (e.g., converted to a uniform size and background color as described above in connection with 504 of FIG. 5) to generate normalized images 1404. As shown in FIG. 14, there is extensive variability amongst the input images with half the images having white bones on black backgrounds, variable collimation configurations, and presence or absence of side markers. Normalized images 1404 were labeled using a detection convolution neural network (e.g., as described above in connection with 508 of FIG. 5) to create pixel label maps 1406. As shown, the constructed label maps used for automatic hand/wrist segmentation cannot be used as a segmentation mask without further processing, because there are frequently false-positive pixels, such as in the 2nd image of pixel label maps 1406. Pixel label maps 1406 were used to create masks 1408 corresponding to the hand represented in each radiograph (e.g., as described above in connection with FIG. 5). Generating masks 1408 included removing false-positive pixels from pixel label maps 1406 by extracting the largest contour and filling the resulting polygon to create uniform masks 1408. Masks 1408 were used to isolate just the hand portion (e.g., by zeroing out the portions outside the mask), which were then centered, resized, and processed (e.g., to remove noise, enhance contrast, etc., as described above in connection with 512 of FIG. 5) to generate processed images 1410. For example, to generate processed images, a vision pipeline can segment the hand and wrist using the generated mask, enhance the bone edges, and denoise the image. As can be seen from FIG. 14, preprocessing the images can convert DICOMS from various vendors with huge differences in appearance, and automatically segment, center, and enhances the images prior to training and deployment of a classification convolution neural network (and/or analysis by that same neural network).

Figure 15:
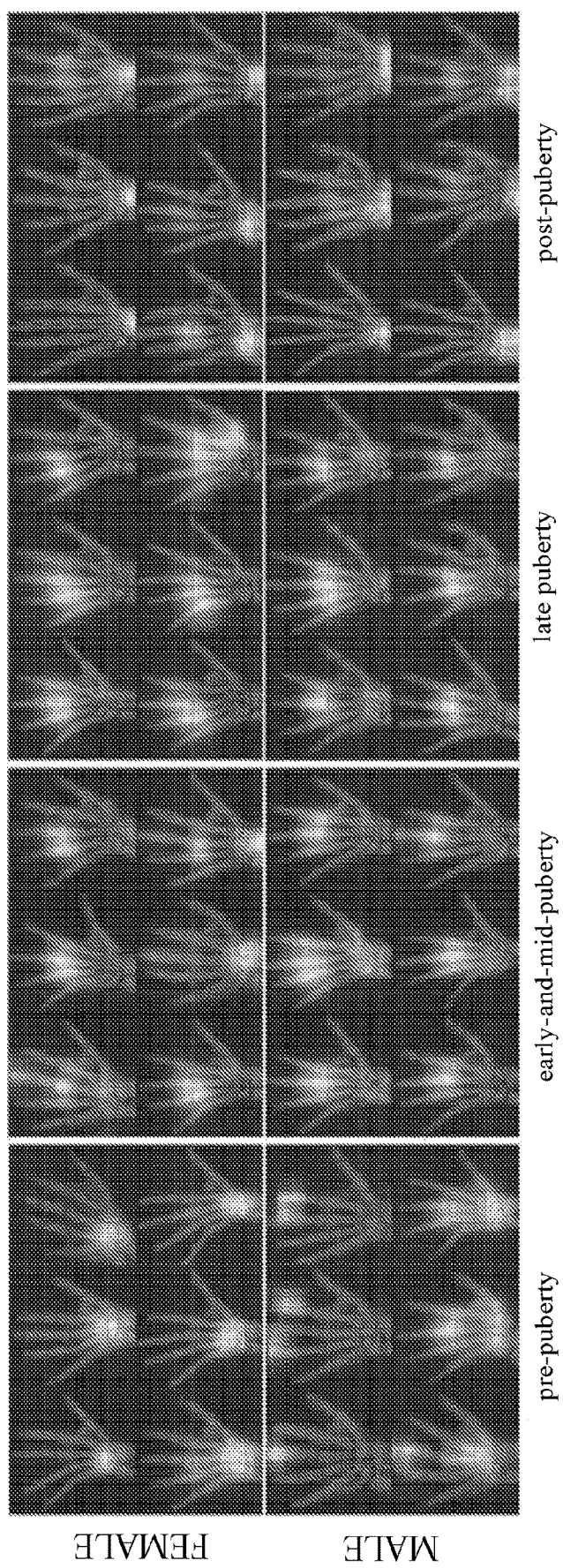
FIG. 15 show an examples of attention maps indicating which areas of a radiograph contributed most to analysis of the bone age represented in accordance with some embodiments of the disclosed subject matter.

FIG. 15 shows examples of attention maps indicating which areas of a radiograph contributed most to analysis of the bone age represented in accordance with some embodiments of the disclosed subject matter. Despite the impressive performance at natural image classification, the inner workings of deep neural networks is not understood. However, several approaches for investigating what neural networks use to perform classification have been explored. As shown in FIG. 15, attention maps were generated using the occlusion method to find which part of an image is locally significant for fine-grained classification. The occlusion method iteratively slides a small patch across the image, passing occluded input images to the forward network, and generating 2-dimensional attention maps based on the change in classification probability as a function of occluder position. Note that in only correctly-classified input images are shown in FIG. 15, which includes representative attention maps for four major skeletal development stages—pre-puberty, early-and-mid-puberty, late-puberty, and post-puberty—highlighting important portions of the image which allowed the trained classification convolution neural network to perform fine-grained classification. In general, the significant regions for each classification partially correspond with the targeted features of each category used in some manual bone age analysis techniques. The prepubertal attention maps focus on carpal bones and mid-distal phalanges, while the early-mid and late-pubertal attention maps focus less on the carpal bones and more on the phalanges, implying that these are more important predictors of bone age than the carpal bones. For post-pubertal attention maps, importance returns to the wrist, where the radial and ulnar physes are the last to close.

In general, attention maps (such as those shown in FIG. 15) reveal key regions similar to what domain experts use to perform conventional bone age assessments, however, it is not certain whether the algorithm uses the exact same features as domain experts. Rather, the attention maps reveal that the important regions of the images being used are similar.

Note that, while GoogLeNet was used as the basis for the network topology for the classification CNN, new neural network architectures more optimized for bone age assessment may yield more accurate results. For example, networks such as GoogLeNet, VGGNet, and ResNet, contain many layers (e.g., 16 to 152), and run the risk of overfitting given the relatively small amount of training images available, and their relative uniformity (all are images of the left hand and wrist of patients). Further, bone ages obtained from previously generated reports may not necessarily reflect the ground truth bone age represented in the radiograph, as bone age assessment is inherently based on subjective analysis of human experts. Additionally, these reports do not provide consistent data; in some radiology reports, bone ages were recorded as single numbers, numerical ranges, or even a time point not included in the original GP atlas. Additionally, Greulich and Pyle's original atlas itself includes standard deviations that range from 8 to 11 months for a given chronological age, reflecting the inherent variation in the study population. Accordingly, not all the ground truths can be assumed as correct. In light of this, training of the classification CNN can be modified to include iterative training by applying varying weights to training images based on confidence levels in the bone age assessment included in them.

The mechanisms described herein can be used for bone age analysis in clinical environments to both more efficiently, more consistently, and/or more accurately perform bone age assessment. For example, in some embodiments, a single bone-age assessment using a preprocessed image can be performed in approximately 10 milliseconds (ms), while preprocessing the image requires an average of 1.71 seconds prior to classification. Most of this time is consumed by the construction of the label map prior to segmentation. The time could be decreased by exploiting a selective search to process only plausible regions of interest. Additionally, instead of preserving aspect ratios and creating a 512×512 pixels image, image warping to a smaller matrix size can reduce the computational time required for segmentation at the cost of eventual output image quality. Although not all stages of preprocessing and bone age assessment can be performed in real time (e.g., <30 ms), net interpretation time is still accelerated compared to conventional assessments, which take 5 minutes on average.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

It should be noted that, as used herein, the term mechanism can encompass hardware, software, firmware, or any suitable combination thereof.

It should be understood that the above described steps of the processes of FIGS. 4-7 can be executed or performed in any order or sequence not limited to the order and sequence shown and described in the figures. Also, some of the above steps of the processes of FIGS. 4-7 can be executed or performed substantially simultaneously where appropriate or in parallel to reduce latency and processing times.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

What is claimed is:

1. A system for generating a bone age assessment, the system comprising:
   at least one hardware processor that is programmed to:
      receive an image that includes a subject's left hand and wrist including a plurality of bones;
      convert the image to a predetermined size;
      identify, without user intervention, a first portion of the image that corresponds to the subject's hand and wrist;
      process the first portion of the image to increase contrast between image corresponding to the plurality of bones, and image data that does not correspond to bones to generate a processed image;
      cause a trained convolution neural network to determine a most likely bone age represented by the plurality of bones based on the processed image;
      receive an indication of the most likely bone age represented by the one or more bones;
      cause the most likely bone age to be presented to a user as the result of a bone age assessment; and cause the most likely bone age and the image to be stored in an electronic medical record associated with the subject.

2. The system of claim 1, wherein the system is a first computing device connected as part of a local area network, the at least one hardware processor is further programmed to:
receive the image from a second computing device connected as part of the local area network;
send the processed image to a remote server that hosts the trained neural network over a wide area network.

3. A system for generating a bone age assessment, the system comprising:
at least one hardware processor that is programmed to:
receive an image that includes a subject's left hand and wrist including a plurality of bones;
convert the image to a predetermined size;
identify, without user intervention, a first portion of the image that corresponds to the subject's hand and wrist;
process the first portion of the image to increase contrast between image corresponding to the plurality of bones, and image data that does not correspond to bones to generate a processed image;
cause a trained convolution neural network to determine a most likely bone age represented by the plurality of bones based on the processed image;
receive an indication of the most likely bone age represented by the one or more bones;
cause the most likely bone age to be presented to a user as the result of a bone age assessment;
cause the most likely bone age and the image to be stored in an electronic medical record associated with the subject;
wherein the at least one hardware processor is further programmed to:
cause the most likely bone age to be presented to the user with a plurality of representative images including a first image that includes features corresponding to the most likely bone age, a second image that includes features corresponding to a second most likely bone age, and a third image that includes features corresponding to a third most likely bone age;
prompt the user to select a bone age represented in the image; and
cause the most likely bone age, the image, and the selected bone age to be stored in the electronic medical record.

4. The system of claim 1, wherein the system is a first computing device connected as part of a local area network, the at least one hardware processor is further programmed to:
receive the image from a second computing device connected as part of the local area network; and
execute the trained neural network to determine the most likely bone age represented by the plurality of bones.

5. The system of claim 4, wherein the at least one hardware processor is further programmed to receive the trained neural network from a remote server over a wide area network.

6. A system for generating a bone age assessment, the system comprising:
at least one hardware processor that is programmed to:
receive an image that includes a subject's left hand and wrist including a plurality of bones;
convert the image to a predetermined size;
identify, without user intervention, a first portion of the image that corresponds to the subject's hand and wrist;
process the first portion of the image to increase contrast between image corresponding to the plurality of bones, and image data that does not correspond to bones to generate a processed image;
cause a trained convolution neural network to determine a most likely bone age represented by the plurality of bones based on the processed image;
receive an indication of the most likely bone age represented by the one or more bones;
cause the most likely bone age to be presented to a user as the result of a bone age assessment;
cause the most likely bone age and the image to be stored in an electronic medical record associated with the subject;
wherein the at least one hardware processor is further programmed to:
cause a second trained convolution neural network to classify a first patch of a second predetermined size, including a first pixel, from the image to determine the likelihood that the first patch includes hand;
cause the second trained convolution neural network to classify a second patch of the second predetermined size, including the first pixel, from the image to determine the likelihood that the second patch includes hand;
label the first pixel as hand based on the likelihood that the first patch includes hand and the likelihood that the second patch includes hand;
label a plurality of pixels as corresponding to hand; and
label a second plurality of pixels as not corresponding to hand.

7. The system of claim 6, wherein the at least one hardware processor is further programmed to:
identify a largest group of contiguous pixels labeled as hand based on labels corresponding to the first pixel and the plurality of pixels;
generate a mask based on the largest group of continuous pixels;
remove image data that does not correspond to the mask; and
center the image that corresponds to the mask.

8. The system of claim 6, wherein the second trained convolution neural network outputs a plurality of likelihoods each corresponding to the presence of a particular type of object in a patch of the second predetermined size, wherein a first likelihood corresponds to the presence of bone, a second likelihood corresponds to the presence of tissue, and the likelihood that a patch includes hand is the sum of the first likelihood and the second likelihood.

9. A system for generating a bone age assessment, the system comprising:
at least one hardware processor that is programmed to:
receive an image that includes a subject's left hand and wrist including a plurality of bones;
convert the image to a predetermined size;
identify, without user intervention, a first portion of the image that corresponds to the subject's hand and wrist;
process the first portion of the image to increase contrast between image corresponding to the plurality of bones, and image data that does not correspond to bones to generate a processed image;

cause a trained convolution neural network to determine a most likely bone age represented by the plurality of bones based on the processed image;
receive an indication of the most likely bone age represented by the one or more bones;
cause the most likely bone age to be presented to a user as the result of a bone age assessment;
cause the most likely bone age and the image to be stored in an electronic medical record associated with the subject
wherein the at least one hardware processor is further programmed to:
receive a set of training images each corresponding to a radiograph of a hand;
receive, for each training image, bone age information indicating the bone age represented in the training image;
convert each training image to the predetermined size;
determine a background color of each training image;
convert a first training image included in the set of training images that has a light background and dark bones to a first normalized training image that has a dark background and light bones;
extract a plurality of samples from a subset of training images included in the set of training images, wherein each sample is a second predetermined size, and corresponds to one of a plurality of object classes;
label each of the plurality samples as corresponding to one of the plurality of object classes;
train a second convolution neural network to determine the likelihood that a submitted patch of the second predetermined size is a member of each of the plurality of object classes using the labeled plurality of samples as training data;
provide a first training image of the predetermined size from the set of training images to the second convolution neural network;
identify a first portion of the first training image that corresponds to hand based on output of the second convolution neural network;
process the first portion to increase contrast between image data corresponding to bones in the first training image and image data that does not correspond to bones to generate a first processed image; and
train the convolution neural network using the first processed image and bone age information indicating the bone age represented in the first training image.

10. The system of claim 9, wherein the at least one hardware processor is further programmed to:
initialize the convolution neural network with a pre-trained model generated using natural images; and
fine-tune one or more hyperparameters of the pre-trained model using the first processed image and bone age information indicating the bone age represented in the first training image.

11. A method for generating a bone age assessment, comprising:
receiving an image that includes a subject's left hand and wrist including a plurality of bones;
converting the image to a predetermined size;
identifying, without user intervention, a first portion of the image that corresponds to the subject's hand and wrist;
processing the first portion of the image to increase contrast between image corresponding to the plurality of bones, and image data that does not correspond to bones to generate a processed image;
causing a trained convolution neural network to determine a most likely bone age represented by the plurality of bones based on the processed image;
receiving an indication of the most likely bone age represented by the one or more bones;
causing the most likely bone age to be presented to a user as the result of a bone age assessment; and
causing the most likely bone age and the image to be stored in an electronic medical record associated with the subject.

12. The method of claim 11, further comprising:
receiving, by a first computing device connected as part of a local area network, the image from a second computing device connected as part of the local area network;
sending the processed image from the first computing device to a remote server that hosts the trained neural network over a wide area network.

13. The method of claim 11, further comprising:
receiving, by a first computing device connected as part of a local area network, the image from a second computing device connected as part of the local area network; and
executing, using the first computing device, the trained neural network to determine the most likely bone age represented by the plurality of bones.

14. The method of claim 13, further comprising receiving the trained neural network from a remote server over a wide area network.

15. A method for generating a bone age assessment, comprising:
receiving an image that includes a subject's left hand and wrist including a plurality of bones;
converting the image to a predetermined size;
identifying, without user intervention, a first portion of the image that corresponds to the subject's hand and wrist;
processing the first portion of the image to increase contrast between image corresponding to the plurality of bones, and image data that does not correspond to bones to generate a processed image;
causing a trained convolution neural network to determine a most likely bone age represented by the plurality of bones based on the processed image;
receiving an indication of the most likely bone age represented by the one or more bones;
causing the most likely bone age to be presented to a user as the result of a bone age assessment;
causing the most likely bone age and the image to be stored in an electronic medical record associated with the subject;
further comprising:
causing a second trained convolution neural network to classify a first patch of a second predetermined size, including a first pixel, from the image to determine the likelihood that the first patch includes hand;
causing the second trained convolution neural network to classify a second patch of the second predetermined size, including the first pixel, from the image to determine the likelihood that the second patch includes hand;
labeling the first pixel as hand based on the likelihood that the first patch includes hand and the likelihood that the second patch includes hand;
labeling a plurality of pixels as corresponding to hand; and
labeling a second plurality of pixels as not corresponding to hand.

16. The method of claim 15, further comprising:
identifying a largest group of contiguous pixels labeled as hand based on labels corresponding to the first pixel and the plurality of pixels;
generating a mask based on the largest group of continuous pixels;
removing image data that does not correspond to the mask; and
centering the image that corresponds to the mask.

17. The method of claim 15, wherein the second trained convolution neural network outputs a plurality of likelihoods each corresponding to the presence of a particular type of object in a patch of the second predetermined size, wherein a first likelihood corresponds to the presence of bone, a second likelihood corresponds to the presence of tissue, and the likelihood that a patch includes hand is the sum of the first likelihood and the second likelihood.

18. The method of claim 15:
receiving a set of training images each corresponding to a radiograph of a hand;
receiving, for each training image, bone age information indicating the bone age represented in the training image;
converting each training image to the predetermined size;
determining a background color of each training image;
converting a first training image included in the set of training images that has a light background and dark bones to a first normalized training image that has a dark background and light bones;
extracting a plurality of samples from a subset of training images included in the set of training images, wherein each sample is a second predetermined size, and corresponds to one of a plurality of object classes;
labeling each of the plurality samples as corresponding to one of the plurality of object classes;
training a second convolution neural network to determine the likelihood that a submitted patch of the second predetermined size is a member of each of the plurality of object classes using the labeled plurality of samples as training data;
providing a first training image of the predetermined size from the set of training images to the second convolution neural network;
identifying a first portion of the first training image that corresponds to hand based on output of the second convolution neural network;
processing the first portion to increase contrast between image data corresponding to bones in the first training image and image data that does not correspond to bones to generate a first processed image; and
training the convolution neural network using the first processed image and bone age information indicating the bone age represented in the first training image.

19. The method of claim 18, further comprising:
initializing the convolution neural network with a pre-trained model generated using natural images; and
fine-tuning one or more hyperparameters of the pre-trained model using the first processed image and bone age information indicating the bone age represented in the first training image.

20. A method for generating a bone age assessment, comprising:
receiving an image that includes a subject's left hand and wrist including a plurality of bones;
converting the image to a predetermined size;
identifying, without user intervention, a first portion of the image that corresponds to the subject's hand and wrist;
processing the first portion of the image to increase contrast between image corresponding to the plurality of bones and image data that does not correspond to bones to generate a processed image;
causing a trained convolution neural network to determine a most likely bone age represented by the plurality of bones based on the processed image;
receiving an indication of the most likely bone age represented by the one or more bones;
causing the most likely bone age to be presented to a user as the result of a bone age assessment;
causing the most likely bone age and the image to be stored in an electronic medical record associated with the subject;
further comprising:
causing the most likely bone age to be presented to the user with a plurality of representative images including a first image that includes features corresponding to the most likely bone age, a second image that includes features corresponding to a second most likely bone age, and a third image that includes features corresponding to a third most likely bone age;
prompting the user to select a bone age represented in the image; and
causing the most likely bone age, the image, and the selected bone age to be stored in the electronic medical record.

21. A non-transitory computer readable medium containing computer executable instructions that, when executed by a processor, cause the processor to perform a method for generating a bone age assessment, comprising:
receiving an image that includes a subject's left hand and wrist including a plurality of bones;
converting the image to a predetermined size;
identifying, without user intervention, a first portion of the image that corresponds to the subject's hand and wrist;
processing the first portion of the image to increase contrast between image corresponding to the plurality of bones, and image data that does not correspond to bones to generate a processed image;
causing a trained convolution neural network to determine a most likely bone age represented by the plurality of bones based on the processed image;
receiving an indication of the most likely bone age represented by the one or more bones;
causing the most likely bone age to be presented to a user as the result of a bone age assessment; and
causing the most likely bone age and the image to be stored in an electronic medical record associated with the subject.

* * * * *